United States Patent [19]

Ishimura et al.

[11] Patent Number: 5,255,681
[45] Date of Patent: Oct. 26, 1993

[54] ULTRASONIC WAVE DIAGNOSING APPARATUS HAVING AN ULTRASONIC WAVE TRANSMITTING AND RECEIVING PART TRANSMITTING AND RECEIVING ULTRASONIC WAVES

[75] Inventors: Toshiro Ishimura, Hachioji; Koichi Matsui, Tokyo; Takahiro Echizenya, Hachioji; Yoshihisa Taniguchi, Hachioji; Akiko Mizunuma, Hachioji, all of Japan

[73] Assignee: Olympus Optical Co., Ltd., Tokyo, Japan

[21] Appl. No.: 799,509

[22] Filed: Nov. 27, 1991

[30] Foreign Application Priority Data

Mar. 20, 1991 [JP] Japan ................... 3-057294
Mar. 20, 1991 [JP] Japan ................... 3-057295
Apr. 2, 1991 [JP] Japan ................... 3-070163
Apr. 18, 1991 [JP] Japan ................... 3-086767
May 2, 1991 [JP] Japan ................... 3-111993

[51] Int. Cl.$^5$ ................................ A61B 8/12
[52] U.S. Cl. .................... 128/660.09; 128/660.07; 128/662.06
[58] Field of Search .............. 128/660.09, 660.08, 128/660.07, 662.06, 661.01, 660.10

[56] References Cited

U.S. PATENT DOCUMENTS

| 4,637,256 | 1/1987 | Sugiyama et al. | 128/660.09 |
| 4,779,624 | 10/1988 | Yokoi | 128/662.06 |
| 4,880,011 | 11/1989 | Imade et al. | 128/662.06 |
| 5,097,709 | 3/1992 | Masuzawa et al. | 128/661.01 |

FOREIGN PATENT DOCUMENTS 0037047 7/1984 European Pat. Off. .
3405537A1 8/1985 Fed. Rep. of Germany .
3914619A1 11/1990 Fed. Rep. of Germany .
2-265536 10/1990 Japan .

Primary Examiner—Kyle L. Howell
Assistant Examiner—George Manuel
Attorney, Agent, or Firm—Armstrong, Westerman, Hattori, McLeland & Naughton

[57] ABSTRACT

The ultrasonic wave diagnosing apparatus of this invention comprises a controlling circuit controlling the rotation, advance and retreat of an ultrasonic wave oscillator, a DC power source feeding an electric power to a DC motor rotating the ultrasonic wave oscillator, a DC motor controlling circuit inputting a controlling signal from the above mentioned controlling circuit and controlling the voltage of the above mentioned DC power source, a photointerrupter detecting the position of the ultrasonic wave oscillator by the advance and retreat, a stepping motor advancing and retreating the above mentioned ultrasonic wave oscillator and a record controlling apparatus controlling an auxiliary memorizing apparatus which can record an ultrasonic wave image obtained by the above mentioned ultrasonic wave oscillator so that, in order to reverse the rotation by inverting the phases of controlling signals A and B of the stepping motor advancing and retreating the above mentioned ultrasonic wave oscillator, a position detecting signal of the above mentioned photointerrupter is input into the above mentioned controlling circuit.

21 Claims, 27 Drawing Sheets

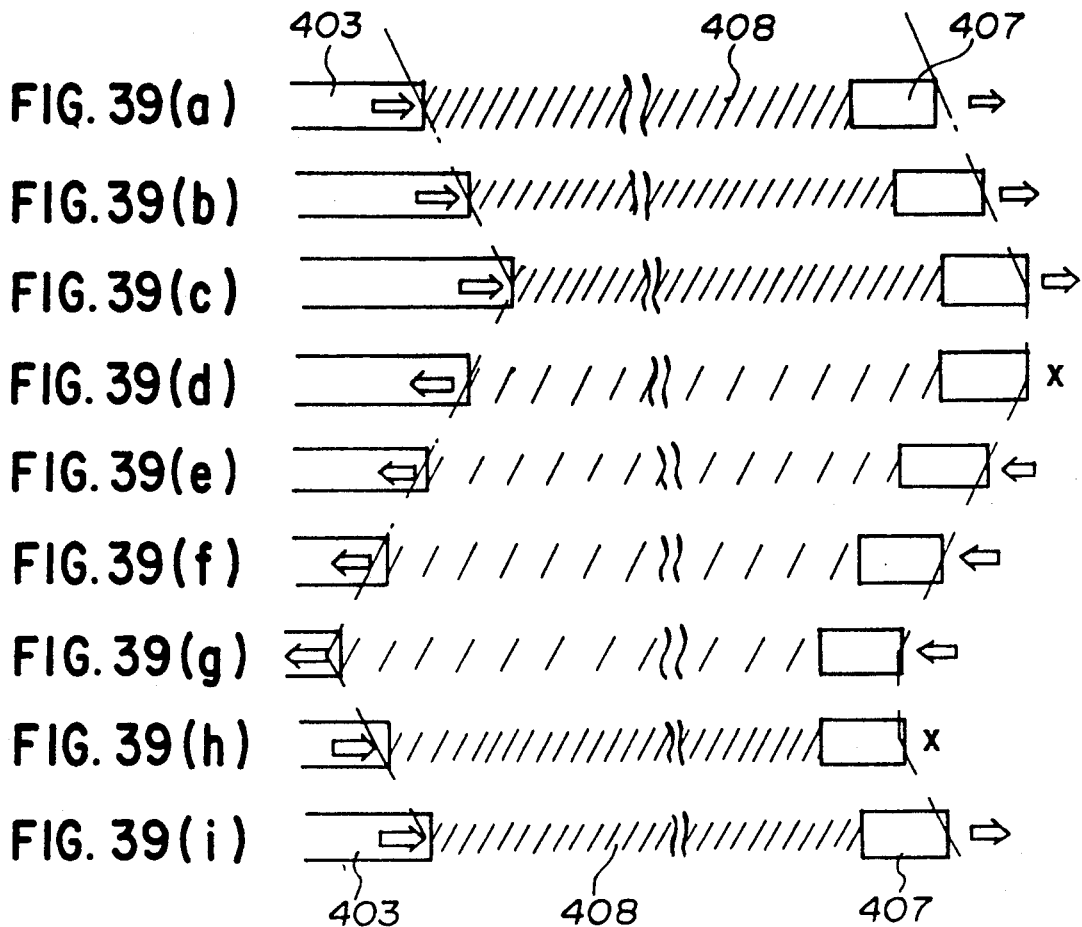
(PRIOR ART)
FIG. 39(a)
FIG. 39(b)
FIG. 39(c)
FIG. 39(d)
FIG. 39(e)
FIG. 39(f)
FIG. 39(g)
FIG. 39(h)
FIG. 39(i)
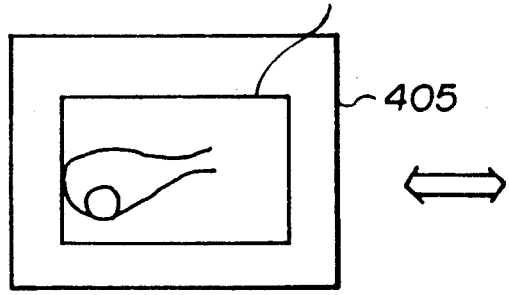
FIG. 40(a)
(PRIOR ART)
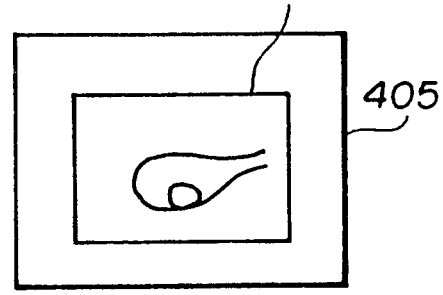
FIG. 40(b)
(PRIOR ART)

ced with encoder 324 for detecting the rotating position of this stepping motor 323.

ULTRASONIC WAVE DIAGNOSING APPARATUS HAVING AN ULTRASONIC WAVE TRANSMITTING AND RECEIVING PART TRANSMITTING AND RECEIVING ULTRASONIC WAVES

BACKGROUND OF THE INVENTION

1. Field of the Invention

This invention relates to ultrasonic wave diagnosing apparatus, more particularly, to an ultrasonic wave diagnosing apparatus scanning three-dimensional ultrasonic waves.

2. Description of Related Art

There are already invented various ultrasonic wave probes which are well-known can be inserted into body cavities to obtain cross-sectioned images within the bodies. Such conventional ultrasonic wave probes typically have a display by means of such single scanning systems as a linear scanning system or a radial scanning system.

However, in the case of observing plaque or the like within a vein, it is desirable to take a three-dimensional image by simultaneously displaying a linear image and a radial image.

Therefore, there is a conventional a method wherein, as shown in FIG. 33(A), by advancing and retreating in each rotation an ultrasonic wave probe 301 having an ultrasonic wave oscillator 302 in one side part, several cross-sectioned images are taken in and processed to display linear images and radial images.

For such an apparatus wherein radial images and linear images can be obtained, an apparatus wherein an ultrasonic wave probe can be made to radially scan and can be moved in the axial direction is disclosed in the publications, for example, of Japanese patent application laid open No. 9439/1982 and Japanese utility model application laid open No. 74108/1988.

Another known scanning system for simultaneously displaying a radial image and a linear image is a spiral system wherein, as shown in FIG. 33(B), the probe 301 is advanced and retreated at any time and is simultaneously rotated.

The present applicant has also suggested, in the publication of Japanese patent application laid open No. 265536/1990, such apparatus wherein the rotating drive and advancing and retreating drive of an ultrasonic wave probe are synchronized with each other to be controlled as is shown in FIGS. 34 and 35.

In a three-dimensional scanning driving part 310 of a prior art example, as shown FIG. 34, an ultrasonic wave oscillator 311 used for transmitting and receiving an ultrasonic wave is connected to a shaft-like drive transmitting part 312, and both are contained within a sheath 313 closed in a spherical tip part. The above-mentioned sheath 313 is provided within its tip a sealing member 314 and O-rings 315 holding the above-mentioned drive transmitting part 312. The space within the tip part of the sheath 313, which is tightly sealed with the above-mentioned sheath 313, sealing member 314 and O-rings 315, is filled with an acoustic medium 316.

The above-mentioned drive transmitting part 312 in the rear end part is extended out of the rear end part of the above-mentioned sheath 313 and is connected to a stepping motor 318 through a connecting part 317. This stepping motor 318 is combined with an encoder 319 detecting the rotating position of the stepping motor 318 and they are both contained and held within a rotating motion part sheath 320.

The above-mentioned rotating motion part sheath 320 is fitted to an advancing and retreating motion transmitting part 321 which is screwed to an advancing and retreating mechanism part 322 consisting of a ball screw. The above-mentioned advancing and retreating mechanism part 322 is connected to a stepping motor 323 driving part so as to be rotated by this stepping motor 323. The above-mentioned stepping motor 323 is combined with an encoder 324 for detecting the rotating position of this stepping motor 323.

The above-mentioned connecting part 317, stepping motor 318, encoder 319, rotating motion part sheath 320, advancing and retreating motion transmitting part 321, advancing and retreating mechanism part 322, stepping motor 323 and encoder 324 are enclosed with the sheath 325 to which is fixed the above-mentioned sheath 313 in a rear end part. The above-mentioned stepping motor 323 is fixed to the above-mentioned sheath 325.

As shown in FIG. 35, the ultrasonic wave probe controlling system comprises a controlling circuit 330 controlling the rotation, advancing and retreating of the ultrasonic wave oscillator 311, a clock oscillator 331 inputting a starting signal str of the ultrasonic wave oscillator 311 and outputting a clock clc, and a delaying circuit 332 inputting the clock clc from the above mentioned clock oscillator 331 and outputting a signal DLY obtained by delaying this clock clc by ¼ period T.

The above-mentioned clock clc and signal DLY are input as two-phase driving signals into the stepping motors 318 and 323 through a switching switch 333, which is controlled by a controlling signal J from the above-mentioned controlling circuit 330 to switch the state where the clock clc is of a phase A and the signal DLY is of a phase B and the state that the clock clc is of the phase B and the signal DLY is of the phase A over to each other.

The phase A, output C of the encoder 319 connected to the above-mentioned stepping motor 318 and the phase Z, output Z output in each rotation are input into the above mentioned controlling circuit 330. In the same manner, the phase A output G and phase Z output H of the encoder 324 connected to the above mentioned stepping motor 323 are input into the above-mentioned controlling circuit 330.

However, even if spiral scanning is made with such three-dimensional ultrasonic wave diagnosing apparatus, a three-dimensionally scanned ultrasonic wave image will be able to be observed only at the time of scanning. In order to process images accurately three-dimensionally by using a computer or the like on the basis of the ultrasonic wave image obtained by the three-dimensional scanning, it is necessary to record the images once at regular intervals in some image recording means.

In order to prepare frame memories as required for the three-dimensional scanning within the ultrasonic wave diagnosing apparatus body, for example, in order to record 200 sheets of an ultrasonic wave image formed of 512×512×8 bits, a recording capacity of 40M bits will be necessary. In order to prepare such a volume of frame memories, a large amount of expensive memories will be required, the ultrasonic wave diagnosing apparatus body will have to be large, the power consumption will be large and the heat generation will be large.

It has also been impossible to continuously memorize images of a plurality of disease examples.

Further, in order to improve the insertability of the above mentioned ultrasonic wave probe into a body cavity, the probe is desired to be small in its outside diameter. For example, in Japanese utility model application laid open No. 141421/1990, there is disclosed an ultrasonic wave probe wherein a member (housing) holding an ultrasonic wave oscillator unit is made slidably adjacent to the sheath inside diameter surface to make the outside diameter of the probe small.

However, in the above-described ultrasonic wave probe wherein the housing holding the ultrasonic wave oscillator unit is made adjacent to the sheath inside diameter surface to make the probe outside diameter small, the case of a structure that an ultrasonic wave transmitting medium for transmitting ultrasonic waves is compactly closed within the sheath, there will be such disadvantages that the above-mentioned housing will act the same as a piston, where the ultrasonic wave transmitting medium between the probe tip and the above-mentioned housing will obstruct the movement in the lengthwise direction of the above mentioned housing and the linear scannability will deteriorate.

In such a case, if the tip of the ultrasonic wave probe is opened in the structure, the above-described disadvantages will be able to be avoided but, in the ultrasonic probe opened at the tip, there will be such fears that a body liquid will enter the probe interior, the sterilizability will deteriorate and the interior structure of such a probe, including the ultrasonic wave oscillator unit, will contact the living body to reduce the electric insulatability.

Now, in the ultrasonic probe scanning system, there are an electronic scanning system and a mechanical scanning system. The ultrasonic wave beam scanning form can be sectioned into a digital system and a linear system.

FIG. 36(a) shows a radial system ultrasonic wave probe A, and FIG. 36(b) shows a linear system ultrasonic wave probe B. In the drawings, the reference numeral 407 represents an ultrasonic wave oscillator and 406 represents a sheath.

An ultrasonic wave probe of a mechanical linear scanning system is disclosed in the publication, for example, of Japanese patent application laid open No. 302836/1988.

The formation of a conventional mechanical linear scanning system ultrasonic wave probe apparatus shall be explained with reference to FIG. 37.

This ultrasonic wave probe apparatus comprises an ultrasonic wave probe 402 to be inserted into a human body 401, a driving part 403 making this ultrasonic wave probe 402 scan ultrasonic wave beams, an ultrasonic wave observing means 404 building an image signal from a received signal and a television monitor 405 depicting an image.

In the above-mentioned ultrasonic wave probe 402, the reference numeral 406 represents a long flexible sheath containing an ultrasonic wave oscillator 407 reciprocatable within its tip. A flexible shaft 408 within this sheath 406 transmits a reciprocating motion generated by the above-mentioned driving part 403 to the above-mentioned ultrasonic wave oscillator 407 to reciprocate this ultrasonic wave oscillator 407 to linearly scan ultrasonic wave beams.

Within the above-mentioned driving part 403, the rotary motion of a motor 409 is converted to a reciprocating motion by a converting mechanism 410, and this reciprocating motion is transmitted to the above mentioned flexible shaft 408. An encoder 411 detects the rotation angle displacement of the motor 409 and, on the basis of this detected result, controls the reversal of the rotating direction, controls the rotation of the motor 409 and corrects the turbulence of an image 405a caused by the rotation dispersion of the motor 409.

In the case of a diagnosis, the above-mentioned ultrasonic wave probe 402 is inserted into an objective position 412 (for example, a total bile duct) within the human body 1. When the above-mentioned ultrasonic wave oscillator 407 is reciprocated by the driving part 403, an ultrasonic wave beam transmitted and received by this ultrasonic wave oscillator 407 will be linearly scanned to obtain a received signal. This received signal is transmitted to the ultrasonic wave observing means 404 and is converted to an image signal.

Then, this image signal is transmitted to the television monitor 405 and, as shown in FIG. 38(a), an ultrasonic wave cross-sectioned image of the position where the ultrasonic wave beam has been scanned will be depicted.

In FIG. 39, the reciprocating motion generated by the driving part 403 and the reciprocating motion of the ultrasonic wave oscillator 407 reciprocated through the flexible shaft 408 are shown along a time series.

As the above mentioned flexible shaft 408 unavoidably extends and contracts, it will contract in the strokes (a) to (c) where the driving part 403 pushes the ultrasonic wave oscillator 407 but will extend in the strokes (e) to (g) where the above-mentioned ultrasonic wave oscillator 407 is pulled.

Therefore, in the strokes (d) and (h) where the push-/pull is reversed, though the above-mentioned driving part 403 is moving, the above mentioned ultrasonic wave oscillator 407 will stop for a moment.

However, in the ultrasonic wave observing means 404, an image signal is built as synchronized with the rotation displacement of the motor 409 of the driving part 403 by the signal of the encoder 411, image flows will be produced in the part where the above-mentioned ultrasonic wave oscillator 407 stops in the ultrasonic wave cross-sectioned image displayed on the monitor 405, that is, as shown in FIG. 38(b), in both end parts of the image 405a.

Thus, in the conventional ultrasonic wave probe apparatus, there have been such problems that no faithful ultrasonic wave cross-sectioned image will be obtained and the diagnosis will be greatly obstructed.

As a counter-measure against them, the movement displacement of the ultrasonic wave oscillator 407 may be directly detected in the tip part of the above-mentioned ultrasonic wave probe 402, it is technically impossible to make the encoder so small as to be able to be mounted within the small diameter ultrasonic wave probe 402.

There is also considered a means of transmitting the image signal to the television monitor 405 from the ultrasonic wave observing means 404 with the signals in both end parts of the image 405a cut but there are problems that the position of the image contents will be different in the going path and returning path of the scanning and, as shown in FIGS. 40(a) and (b), the image 5a will seem to rock to the right and left with the reciprocation of the ultrasonic wave oscillator 407.

As described above, there have been such problems that, by conventional techniques the image flows in both end parts of the image 405a can not be effectively removed and the disadvantages in the diagnosis cannot be solved.

SUMMARY OF THE INVENTION

An object of the present invention is to provide an ultrasonic wave diagnosing apparatus wherein cross-sectioned images at regular intervals can be automatically taken in and can be accurately processed to be three-dimensional images.

Another object of the present invention is to provide an ultrasonic wave probe wherein the movement in the linear direction of a housing holding an ultrasonic wave oscillator unit can be made smooth and the scannability can be improved.

Further, another object of the present invention is to provide an ultrasonic wave diagnosing apparatus wherein image flows are removed by a simple and effective method.

The ultrasonic wave diagnosing apparatus of the present invention comprises an ultrasonic wave probe having an ultrasonic wave transmitting and receiving part which can be rotated, advanced and retreated and transmits and receives ultrasonic waves; a first driving means rotating this ultrasonic wave transmitting and receiving part; a second driving means advancing and retreating this ultrasonic wave transmitting and receiving part; an auxiliary recording means recording signals from this ultrasonic wave transmitting and receiving part; and a record controlling means outputting to the above-mentioned auxiliary recording means a record controlling signal synchronized with the above-mentioned first driving means and second driving means.

BRIEF DESCRIPTION OF THE DRAWINGS

FIG. 1 is a formation diagram showing the formation of an ultrasonic wave diagnosing apparatus.

FIG. 2 is an explanatory view for explaining the recorded state of a cross-sectioned image on a frame memory at the time of a renewed recording.

FIG. 3 is an explanatory view for explaining the recorded state of a cross-sectioned image on a frame memory at the time of a superimposed recording.

FIG. 5 is a cross-sectioned view showing the formation of an ultrasonic wave probe driving part.

FIG. 6 is a perspective view showing the appearance of a photointerrupter.

FIG. 7 is a block diagram showing an ultrasonic wave probe controlling system.

FIG. 8 is an explanatory view for explaining input and output signals of a microcomputer.

FIG. 9 is a timing chart showing the timing of input and output signals of the microcomputer.

FIG. 10 is a timing chart showing the timing of input and output signals of a microcomputer of the first modification.

FIG. 11 is an explanatory view for explaining input and output signals of a microcomputer of the second modification.

FIG. 13 is an appearance view showing a schematic formation of an ultrasonic wave diagnosing apparatus.

FIG. 14 is an explanatory view for explaining an indicator lamp fitted to the surface panel of a three-dimensional scanning apparatus.

FIG. 15 is a schematic formation view of an ultrasonic wave probe scanning driving system.

FIG. 16 is an explanatory view showing the formation of an ultrasonic wave probe shaft connecting part.

FIG. 17 is a sectioned view in the axial direction of the sheath of the ultrasonic wave probe.

FIG. 18 is a sectioned view in the direction intersecting at right angles with the sheath axis of an ultrasonic wave probe.

FIG. 19 is a sectioned view in the direction intersecting at right angles with the sheath axis of an ultrasonic wave probe of the first modification.

FIG. 20 is a sectioned view in the direction intersecting at right angles with the sheath axis of an ultrasonic wave probe of the second modification.

FIGS. 21 to 24(a), 24(b) relate to the seventh embodiment of the present invention.

FIG. 21 is a general schematic view of an ultrasonic wave diagnosing apparatus.

FIG. 22 is a longitudinally sectioned view of the tip part of an ultrasonic wave probe.

FIG. 23(a)–(f) show longitudinally sectioned views showing the operation of the ultrasonic wave probe along the time series.

FIGS. 24(a), 24(b) show diagrams showing the variations of multiplex echoes detected by an ultrasonic wave observing means.

FIG. 25 is a longitudinally sectioned view of the tip part of the ultrasonic wave probe corresponding to FIG. 22.

FIG. 26 is a diagram showing the variation of the multiplex echo corresponding to FIG. 24(b).

Figure 28:
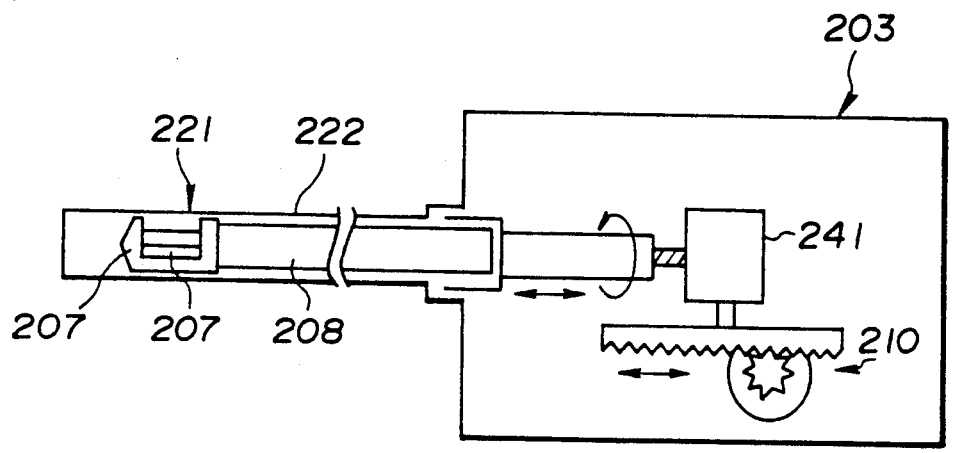
Figure 29:
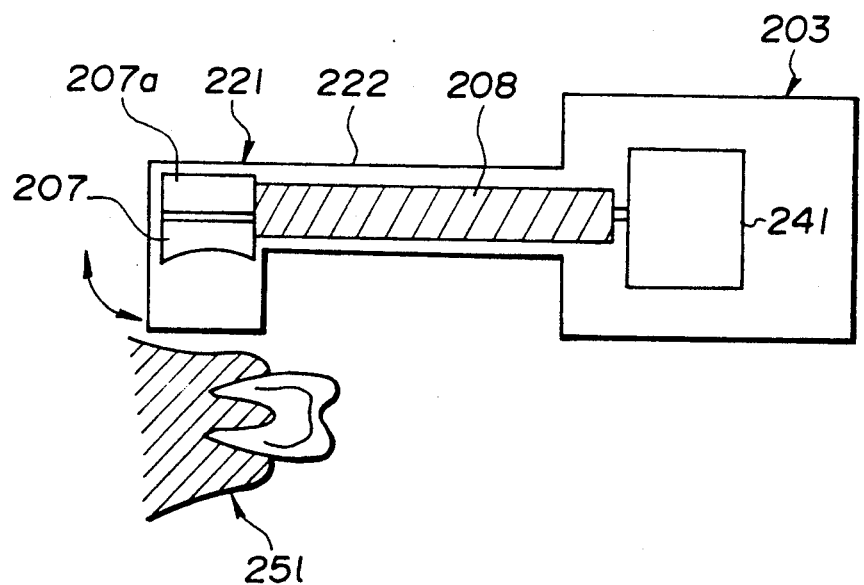

Each of FIGS. 28 and 29 is a schematic view of an essential part of an ultrasonic wave diagnosing apparatus by another mode.

Figure 30:
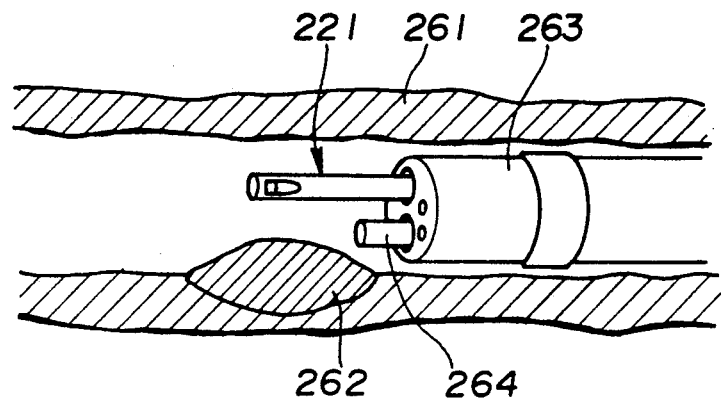

FIG. 30 is a schematic view of a mode of the ultrasonic wave probe according to the present invention as used together with a cauterizing laser probe.

Figure 31:
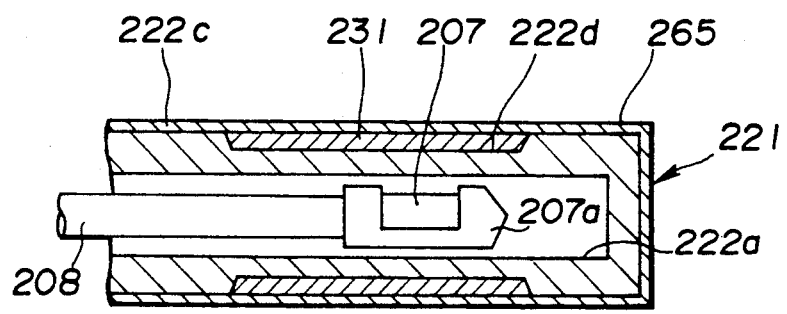

FIG. 31 is a longitudinally sectioned view of the tip part of the ultrasonic wave probe in FIG. 30.

Figure 32:
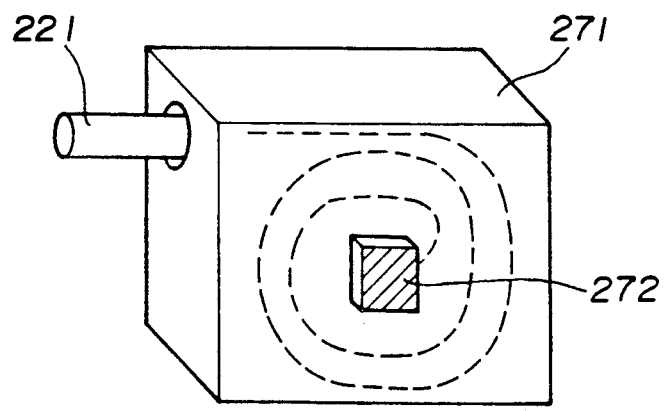

FIG. 32 is a perspective view of an essential part of an ultrasonic wave diagnosing apparatus by another mode.

FIGS. 33A, 33B to 40 relate to prior art examples.

Figure 33A:
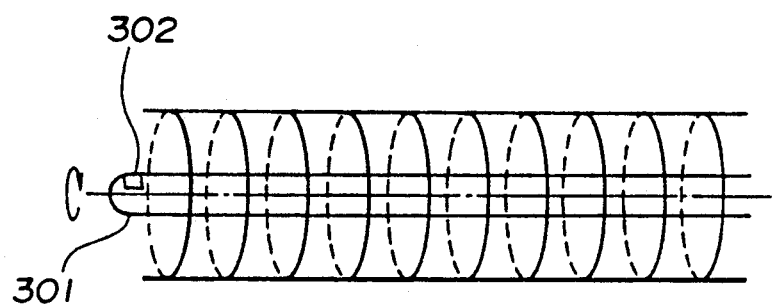
Figure 33B:
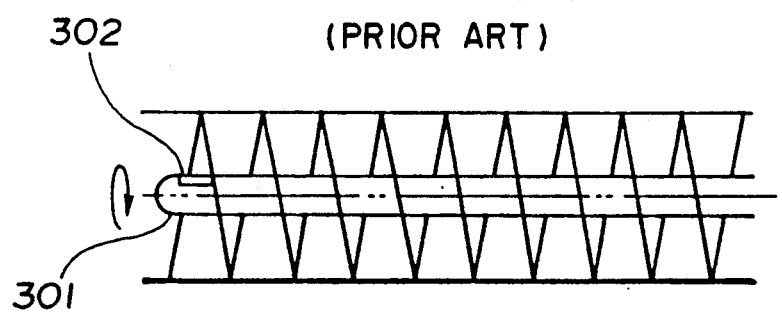

FIGS. 33A, 33B are an explanatory view for explaining a scanning system of a prior art example for obtaining a radial image and linear image.

Figure 34:
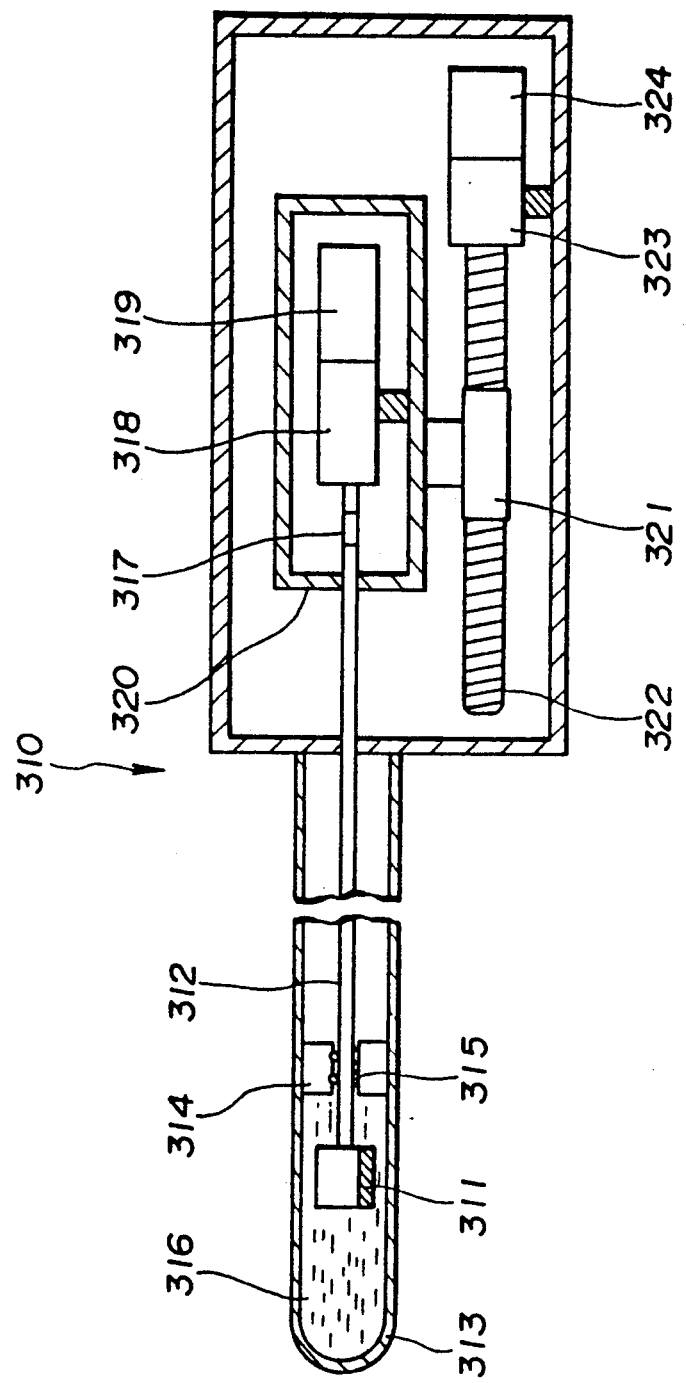

FIG. 34 is a sectioned view showing the formation of an ultrasonic wave probe driving part.

Figure 35:
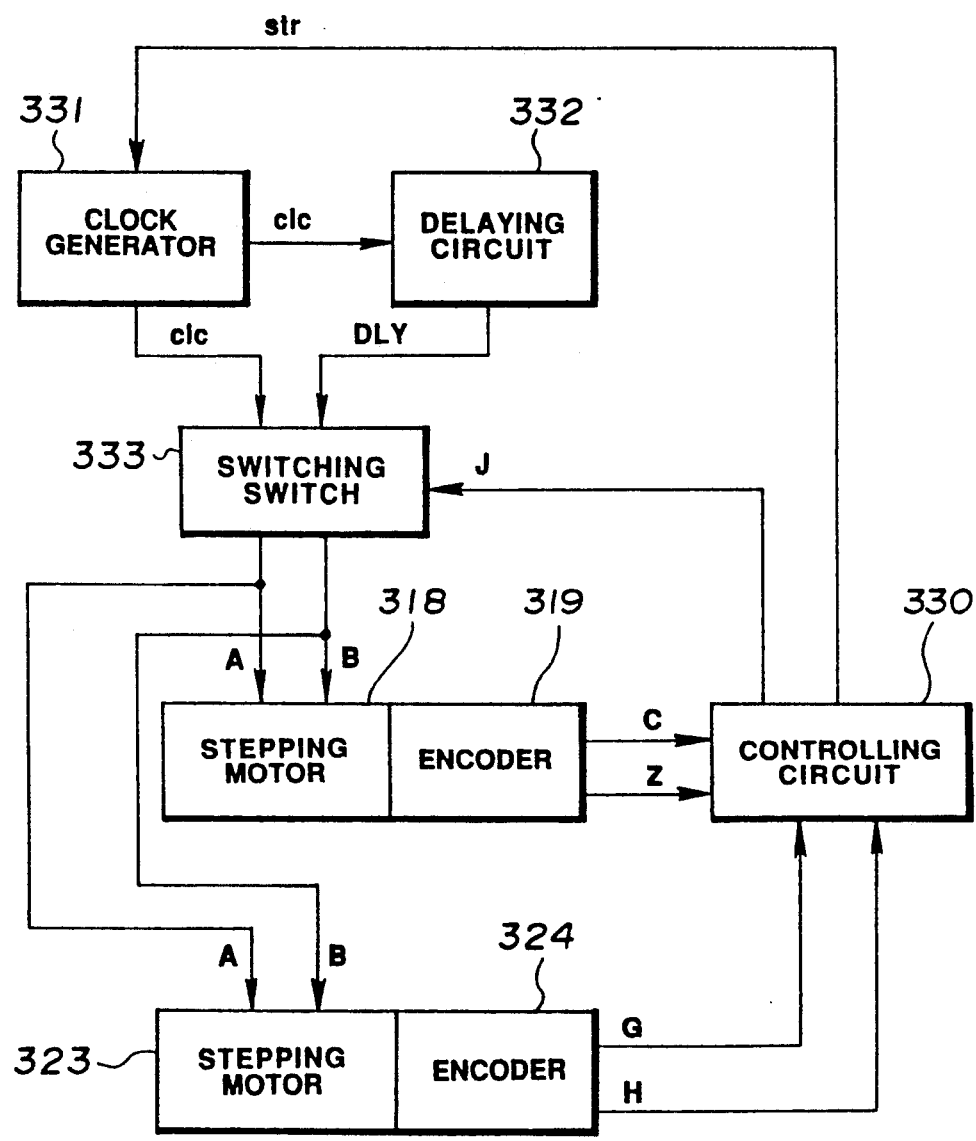

FIG. 35 is a block diagram showing an ultrasonic wave probe controlling system.

Figure 36A:
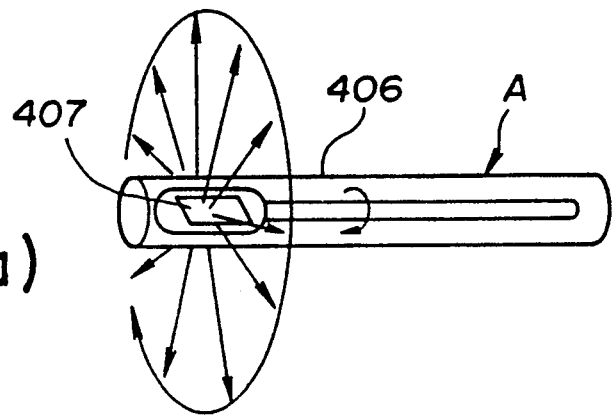
Figure 36B:
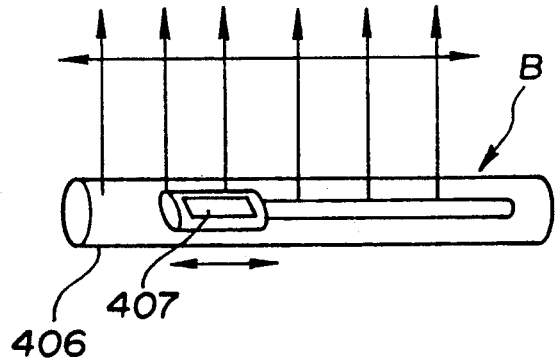

FIGS. 36a, 36b are an explanatory view showing sections by an ultrasonic wave probe scanning system.

Figure 37:
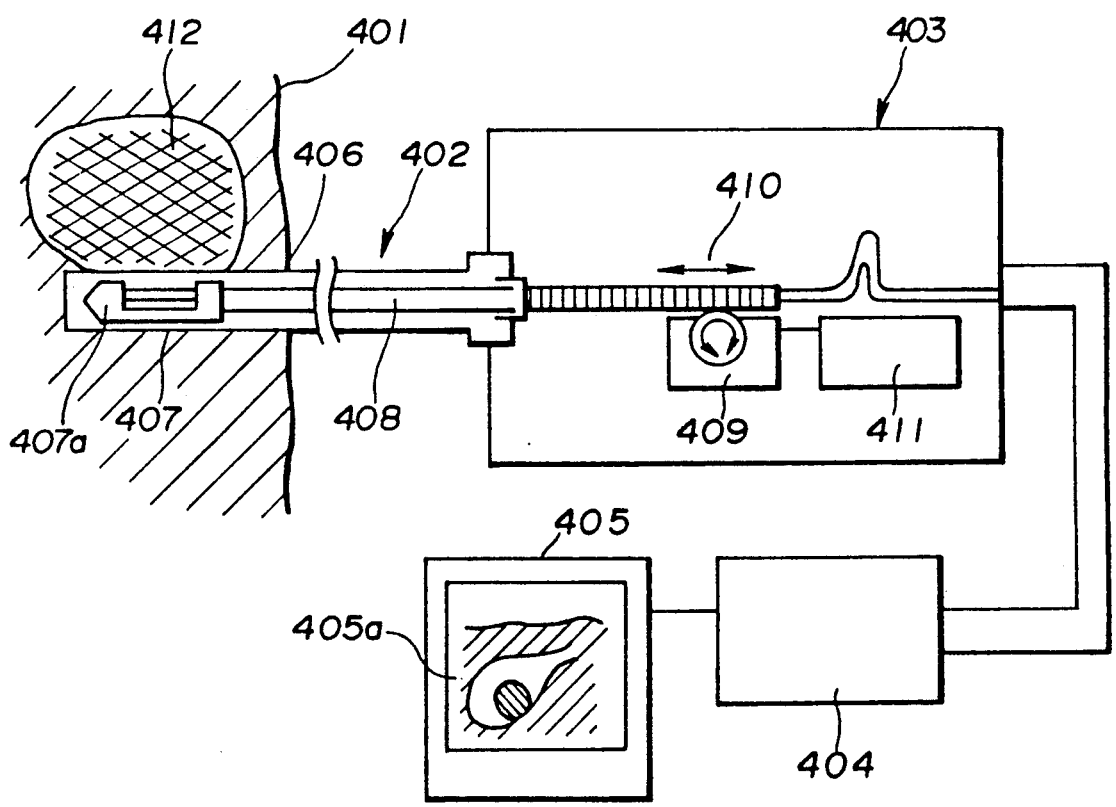

FIG. 37 is a formation diagram showing the general formation of an ultrasonic wave diagnosing apparatus.

Figure 38A:
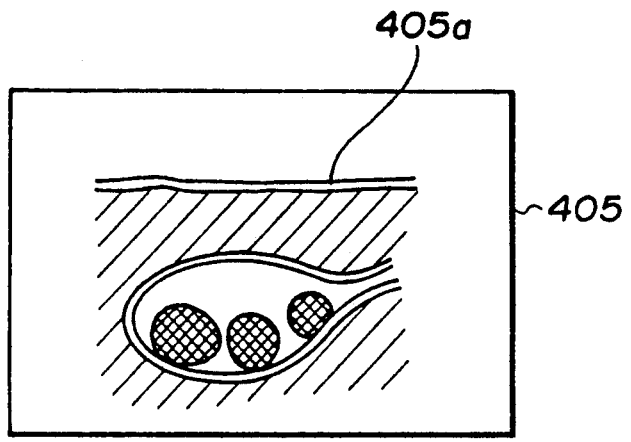
Figure 38B:
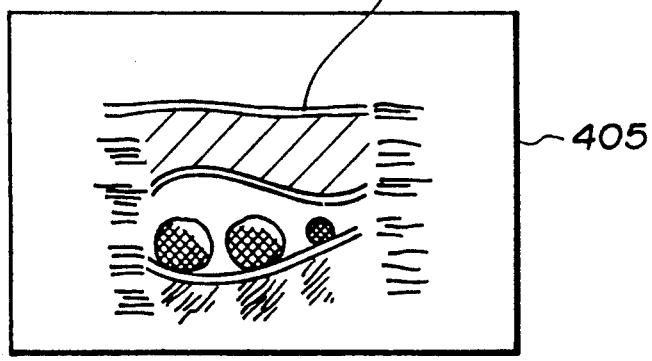

FIGS. 38a, 38b show explanatory views showing ultrasonic wave cross-sectioned images.

FIGS. 39(a)–39(i) are an explanatory diagram showing a time series of an ultrasonic wave probe.

FIGS. 40(A) and 40(B) are an explanatory view showing an ultrasonic wave cross-sectioned image as moved to the right and left.

DETAILED DESCRIPTION OF THE PREFERRED EMBODIMENTS

Figure 1:
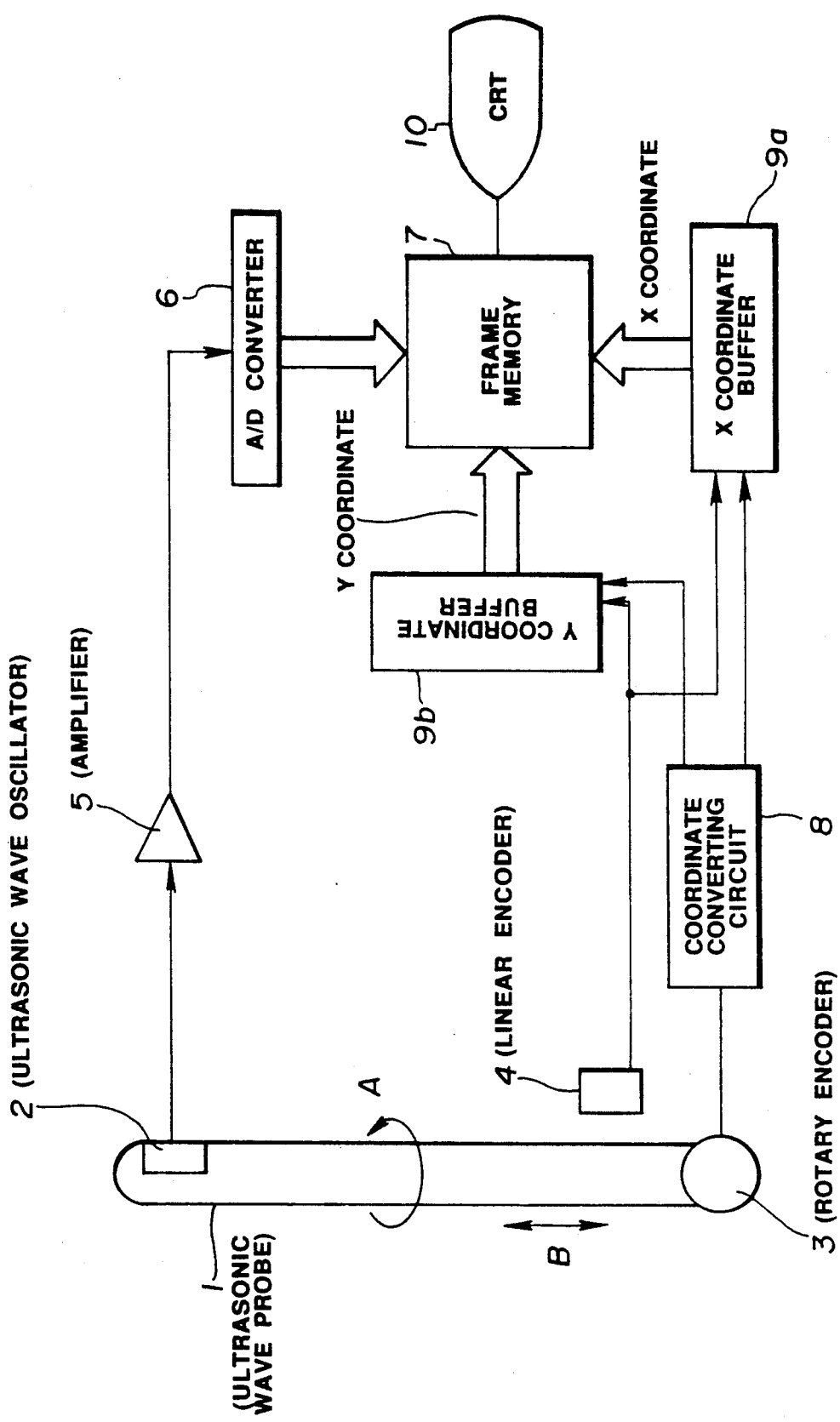
FIGS. 1 to 3 relate to the first embodiment of the present invention.

FIG. 1 is a diagram showing the formation of the first embodiment of the ultrasonic wave diagnosing apparatus of the present invention. In this embodiment, an ultrasonic wave oscillator 2 is fitted to the tip part of an ultrasonic wave probe 1 to which are connected a rotary encoder 3 detecting the rotating angle (indicated by the arrow A) of the ultrasonic wave oscillator 2 and a linear encoder detecting the linear moving distance (indicated by the arrow B) in each scanning by the ultrasonic wave probe 1. An amplifier 5, A/D converter 6 and frame memory 7 are sequentially connected to the ultrasonic wave oscillator 2. The data signal relating to the ultrasonic wave cross-sectioned image obtained by the scanning (radial scanning in this embodiment) by the ultrasonic wave oscillator 2 is amplified and A/D converted and is then input into a later-described address of the frame memory 7 as luminance information. On the other hand, to the rotary encoder 3 are connected an X coordinate buffer 9a and Y coordinate buffer 9b through a coordinate converting circuit 8 and to a linear encoder 4 are directly connected an X coordinate buffer 9a and Y coordinate buffer 9b wherein, when the X and Y coordinates obtained by converting the rotating angle of the ultrasonic wave oscillator 2 with the coordinate converting circuit 8 and the linear moving distance of the ultrasonic wave probe 1 are input, the offset value of the displaying origin position, that is, of the origin position set in the ultrasonic wave cross-sectioned layer image will be determined and, on the basis of this displaying origin position, the X coordinate and Y coordinate of the data signal relating to the ultrasonic wave cross-sectioned image will be input into the frame memory 7. In the frame memory 7, the data signal relating to the above-mentioned ultrasonic wave cross-sectioned image will be recorded in the address corresponding to the X and Y coordinates and is output to a displaying apparatus 10 (CRT in this embodiment) as a standard television signal to be a three-dimensional ultrasonic wave signal.

The operation of this embodiment shall be explained in the following. The ultrasonic wave probe 1 is rotatively driven and linearly driven by a driving means not illustrated. In such case, the ultrasonic wave oscillator 2 will radially scan with the rotation (indicated by the arrow A in FIG. 1) of the ultrasonic wave probe 1 and, as synchronized with the output signal of the rotary encoder 3, one sheet of an ultrasonic wave cross-sectioned image of a B mode will be determined in each rotation. Here, in the coordinate converting circuit 8, on the basis of the rotation angle detected by the rotary encoder 3 and the elapsing time since the ultrasonic wave oscillator 2 transmits the ultrasonic wave, the X and Y coordinates are generated and, in the X and Y coordinate buffers 9a and 9b, these X and Y coordinates and the offset values of the above-mentioned displaying origin positions determined in response to the linear moving distance in each scanning by the ultrasonic probe 1 as detected by the linear encoder 4 are respectively added.

Figure 2:
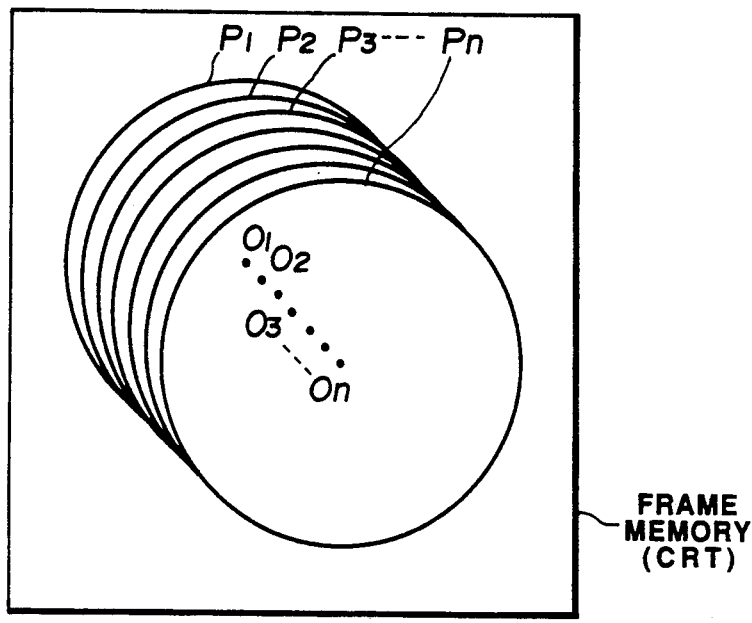

As shown in FIG. 2, these offset values make the displaying origin positions O1, O2, ... and On of a plurality of B mode ultrasonic wave cross-sectioned images P1, P2, ... and Pn such values as move as illustrated, for example, from the left upward direction toward the right downward direction on the frame memory 7. Therefore, the echo signal of a transmitted ultrasonic wave received by the ultrasonic wave oscillator 2, amplified by the amplifier 5 and digitized by the A/D converter 6, that is, the data signal relating to the cross-sectioned image P1 is recorded (written) into the address corresponding to the X and Y coordinates generated from the coordinate converting circuit 8 on the basis of the origin position O1. The case of a renewed recording is shown in this FIG. 2 but the case of a superimposed recording is as in FIG. 3.

The data signal relating to the cross-sectioned image P2 obtained in the next radial scanning accompanying the linearity of the ultrasonic wave probe 1 is recorded in the address corresponding to the X and Y coordinates generated from the coordinate converting circuit 8 on the basis of the origin position O2 but, even if the cross-sectioned image P2 is of substantially the same shape as of the cross-sectioned image P1 but, as the X and Y coordinates of the writing position for the above-described offset value are different, they will not be overlapped but will be recorded as displaced from the P1.

Figure 3:
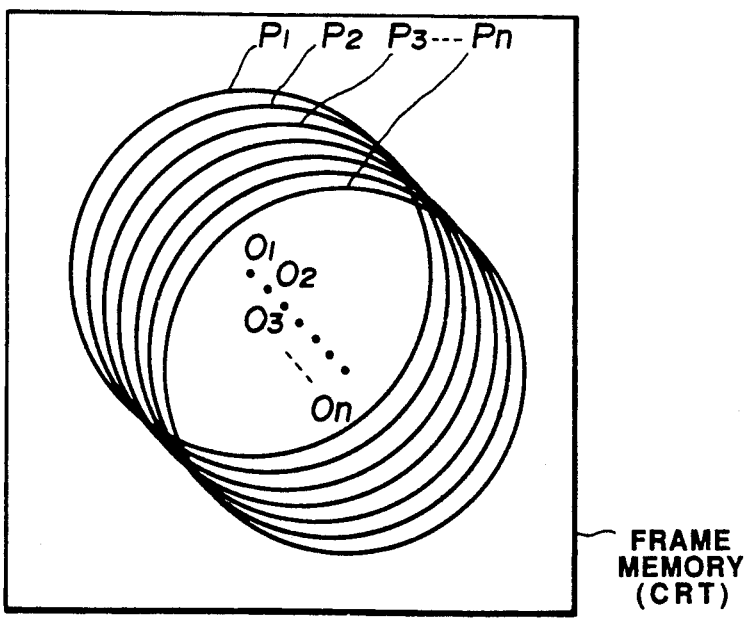

When the cross-sectioned images P3, P4, ... and Pn are sequentially recorded and are video-displayed in the CRT 10 in the same manner in the following, at the scanning stopping time point and therefore at the record stopping time point, the B mode cross-sectioned image Pn radially scanned last in the case of the renewed recording will be all recorded but only a part of the cross-sectioned image before that will remain, an ultrasonic wave image having such depth as has a shade (thickness) in the oblique direction added to the cross-sectioned image Pn as shown in FIG. 2 will be obtained and the object will be able to be three-dimensionally displayed. In this case, even if the number of sheets of the cross-sectioned image is less than one frame, the object in the range of only the obtained cross-sectioned image will be able to be three-dimensionally displayed. Also, in the case of a superimposed recording, in the same manner, such three-dimensional ultrasonic wave image as is shown in FIG. 3 will be obtained. As the above mentioned offset value is made proportional to the linear moving distance of the ultrasonic wave probe 1, even if the linear moving distance corresponding to one radial scanning is dispersed and therefore the ultrasonic wave probe moving speed is dispersed, the displaying origin position of the cross-sectioned image will be changed in response to them and therefore the ultrasonic wave image of the CRT 10 will not be distorted.

By thus using only one frame memory, without operating as in the conventional example, a three-dimensional ultrasonic wave image can be obtained and an ultrasonic wave diagnosing apparatus low in cost and obtained in real time can be provided.

Figure 4:
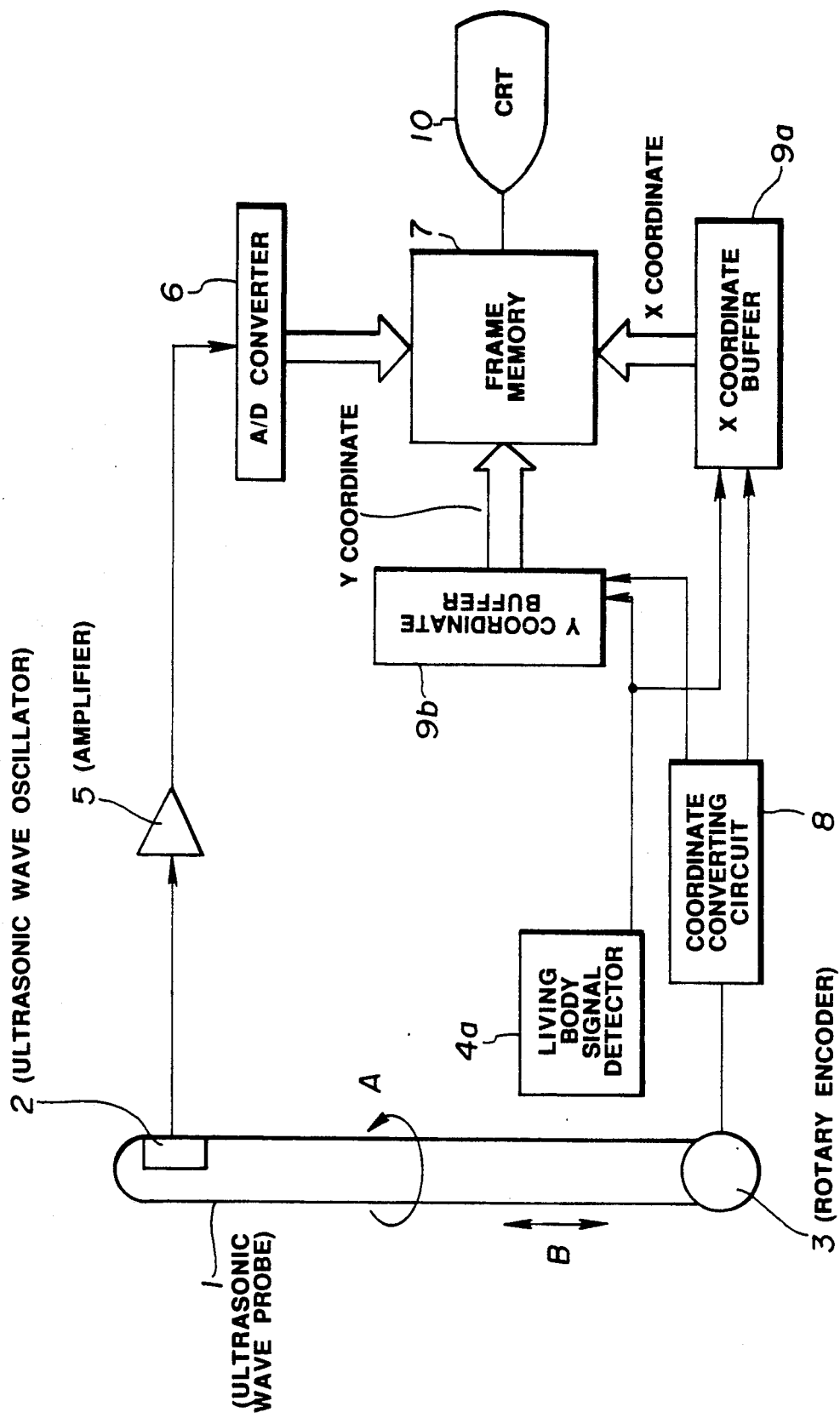
FIG. 4 is a formation diagram showing the formation of an ultrasonic wave diagnosing apparatus relating to the second embodiment.

FIG. 4 is a diagram showing the formation of a second embodiment of the ultrasonic wave diagnosing apparatus of the present invention. The same parts as of the first embodiment shall bear the same reference numerals. The difference of this second embodiment from the first embodiment is that a living body signal detector 4a is used instead of the linear encoder 4 detecting the linear moving distance of the ultrasonic wave probe 1. Other parts are the same.

This living body signal detector 4a is to detect such living body signal having a periodicity as, for example, a pulse signal used in an electrocardiogram. In this embodiment, on the basis of this living body signal, the above described offset values of the X and Y coordinates are varied (by the way, if the pulse signal from the electrocardiogram apparatus is used, the body signal detector will be able to be omitted).

In this embodiment, as described above, the offset value of the displaying origin position is determined by the above mentioned living body signal but, as this living body signal has a periodicity, at the time of the linear drive of the ultrasonic wave probe 1, under the prerequisite that the speed of this linear drive should be substantially constant, this living body signal will be able to be used instead of the linear moving distance in each scanning detected by the linear encoder. The same as in the first embodiment, a three-dimensional ultrasonic wave image can be obtained and an ultrasonic wave diagnosing apparatus low in the price and high in the real time can be provided.

Further, in this embodiment, in case such organ fast in the movement as, for example, a heart is located in the diagnosing part, cross-sectioned images of only the same phase (for example, at the time of the inflation) of the pulsation of the heart will be able to be continuously obtained. Therefore, an examined object located near an organ fast in the movement can be three-dimensionally displayed without being influenced by the operation of the organ fast in the movement.

The formation of an ultrasonic wave diagnosing apparatus driving system of the third embodiment of the present invention shall be explained with reference to FIGS. 5 and 6.

Figure 5:
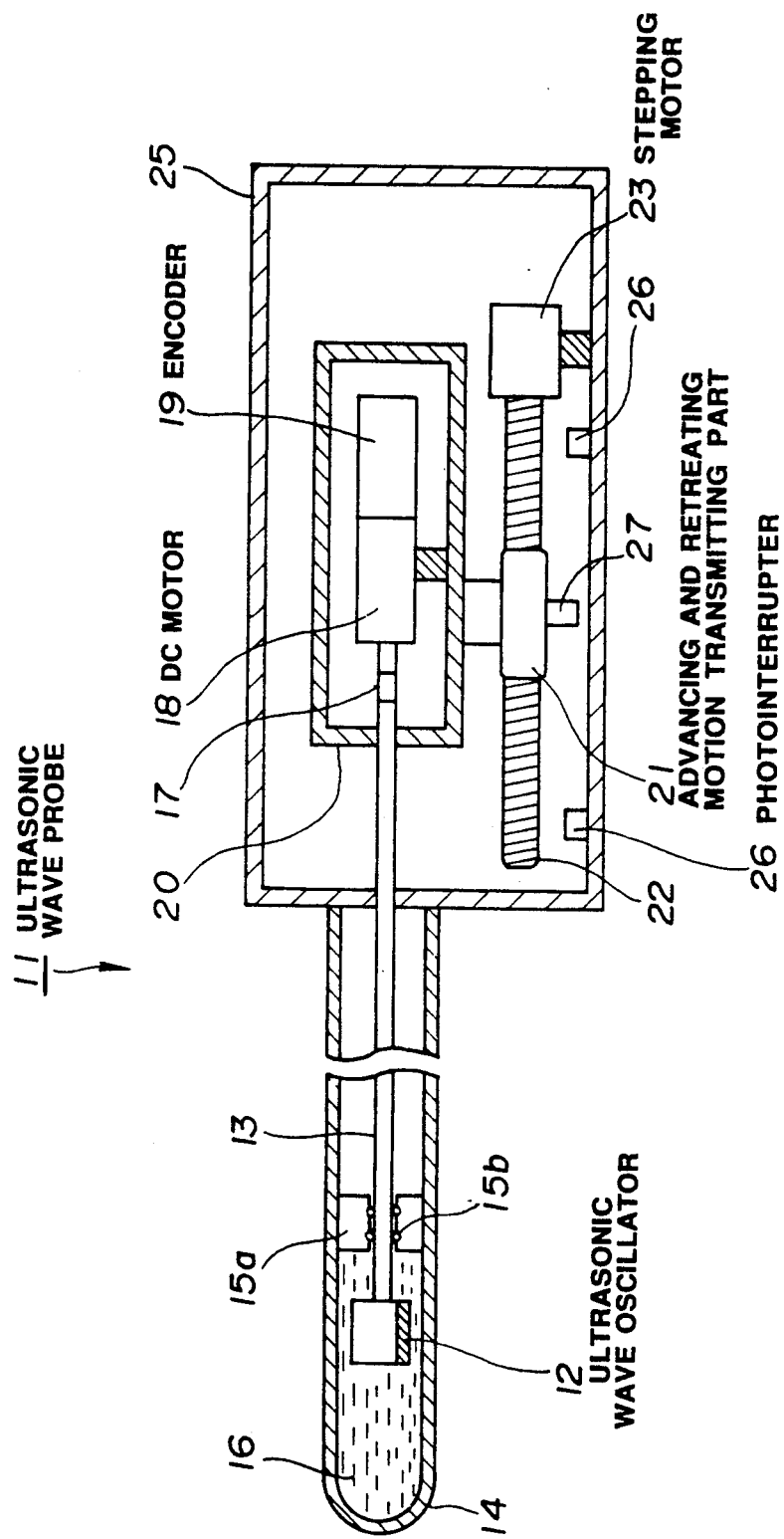
FIGS. 5 to 11 relate to the third embodiment of the present invention.

As shown in FIG. 5, in an ultrasonic wave diagnosing apparatus ultrasonic wave probe 11 made fine in the outside diameter to improve the insertability into a body cavity, mentioned in the publication, for example, of Japanese utility model application laid open No. 141421/1990 and having an ultrasonic wave oscillator unit holding member (housing) slidably adjacent to the inside diameter surface of a sheath, an ultrasonic wave oscillator 12 to be an ultrasonic wave transmitting and receiving part is connected to a shaft-like drive transmitting part 13 and these are contained within the sheath 14 closed in the tip part to be spherical. The above mentioned sheath 14 is provided on the tip side within it with a sealing member 15 and O-rings 15b holding the above mentioned drive transmitting part 13. The space within the sheath 14 tip part tightly closed by the above mentioned sheath 4, sealing member 15a and O-rings 15 is filled with an acoustic medium 16. By the way, the above mentioned drive transmitting part 13 and sheath 14 may be flexible.

The above mentioned drive transmitting part 13 in the rear end part is extended out of the above mentioned sheath 14 in the rear end part and is connected to a DC motor 18 through a connecting part 17. This DC motor 18 is mechanically connected with an encoder 19 detecting the rotating position of the DC motor 18 and these are contained and held within a rotating motion part sheath 20. The ultrasonic wave oscillator 12 is rotated and driven by the DC motor 18 through the drive transmitting part 13 so that the rotating motion of the DC motor 18 may be transmitted to the encoder 19. By the way, a stepping motor may be used instead of the DC motor 18.

The above mentioned rotating motion part sheath 20 is fitted to the advancing and retreating motion transmitting part 21 which is screwed to an advancing and retreating part 22 consisting of a ball screw and is provided with a light shielding plate 27. The above mentioned advancing and retreating mechanism part 22 is connected to a stepping motor 23 driving part so as to be rotated by this stepping motor 23.

The above mentioned connecting part 17, DC motor 18, encoder 19, rotating motion part sheath 20, advancing and retreating motion transmitting part 21, advancing and retreating mechanism part 22 and stepping motor 23 are enclosed with the sheath 25 to which is fixed the above mentioned sheath 14 at the rear end. Also, the above mentioned stepping motor 23 is fixed to the above mentioned sheath 25 to which photointerrupters 26 detecting the movement of the above mentioned advancing and retreating motion transmitting part 21 are further fixed in the positions corresponding to both ends of the advancing and retreating mechanism part 22.

Figure 6:
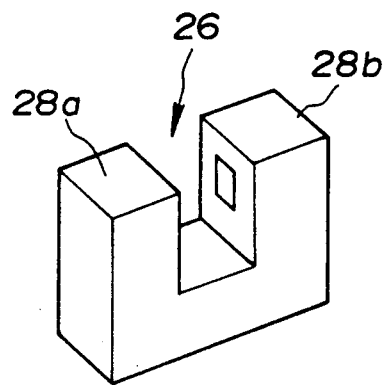

In this photointerrupter 26, as shown in FIG. 6, a light emitting part 28a and a light receiving part 28b are opposed to each other with a slit between them. Usually, by the light emission of an LED within this light emitting part 28a, a phototransistor within the light receiving part 28b is made conductive. When the above mentioned light shielding plate 27 enters the slit between the light emitting part 28a and light receiving part 28b, the light emission of the LED within the light emitting part 28a will be intercepted and the phototransistor will become non-conductive.

Therefore, for example, when the above mentioned advancing and retreating motion transmitting part 21 advances and the above mentioned light shielding plate 27 fixed to the above mentioned advancing and retreating motion transmitting part 21 enters the slit of the photointerrupter 26, the phototransistor which has been conductive of the light receiving part 28b of the photointerrupter 26 will become non-conductive so that the advancing and retreating motion transmitting part 21 may be sensed to have come to the front end part of the advancing and retreating mechanism part 22.

That is to say, by monitoring the conductive/nonconductive state of the phototransistor of the light receiving part 28b of the photointerrupter 26, the movement of the advancing and retreating motion transmitting part 21 to the front and rear end parts of the advancing and retreating mechanism part 22 can be sensed.

The formation of the ultrasonic wave diagnosing apparatus controlling system of the third embodiment shall be explained in the following with reference to FIGS. 7 to 9.

Figure 7:
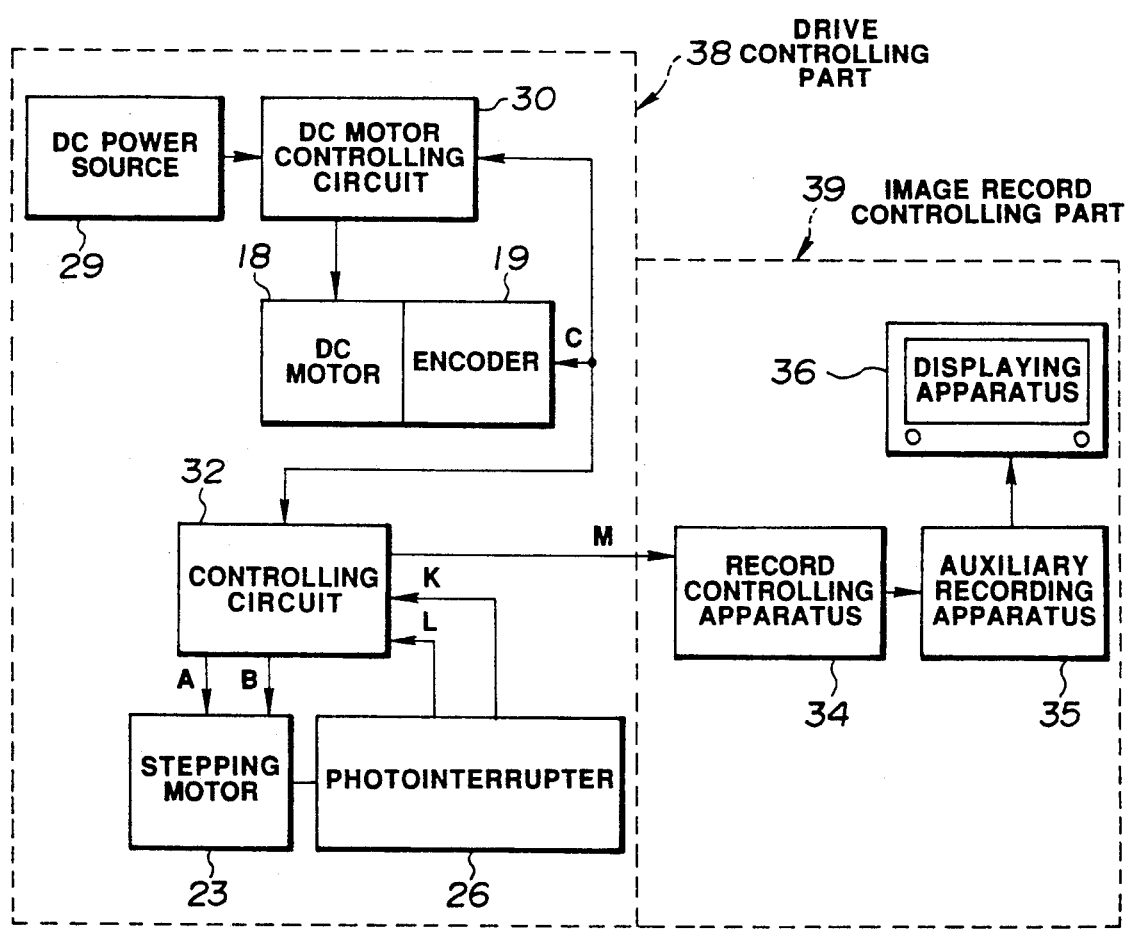

As shown in FIG. 7, the ultrasonic wave diagnosing apparatus is formed of a drive controlling part 38 and an image record controlling part 39. This drive controlling part 38 comprises a controlling circuit 32 controlling the rotation, advance and retreat of the ultrasonic wave oscillator 12, a DC power source 29 feeding an electric power to the DC motor 18 and a DC motor controlling circuit 30 inputting a controlling signal from the above mentioned controlling circuit 32 and controlling the DC motor 18 by controlling the voltage of the above mentioned DC power source 219.

As the phase A signal C output by the above mentioned encoder 19 is input in this DC motor controlling circuit 30 and the period of the phase A signal C varies in response to the rotating speed of the DC motor 18, by controlling the motor driving voltage in response to the period variation of the phase A signal C, the rotation of the DC motor 8 is kept always constant.

Also, the phase A signal C output by the above mentioned encoder 9 is input simultaneously into the above mentioned controlling circuit 32 and this controlling circuit 32 divides the frequency of the phase A signal C and produces the controlling signals A and B of the stepping motor 23.

Further, into this controlling circuit 32 are also input position detecting signals K and L of the photointerrupters 26. By reversing the rotation of the stepping motor 23 by inverting the phases of the controlling signals A and B of the stepping motor 23, the advance and retreat of the above mentioned advancing and retreating motion transmitting part 21 are switched over to each other.

A synchronizing signal M from this controlling circuit 32 is output to a record controlling apparatus 34 formed, for example, of a personal computer. This record controlling apparatus 34 connects such auxiliary memorizing apparatus 35 which can record images as, for example, a photodisc through such general-purpose interface as. for example, an RS-232C or GP-IB so that this auxiliary memorizing apparatus 35 may be controlled.

This record controlling apparatus 34 as synchronized with the synchronizing signal M can transmit a writing in command to the auxiliary memorizing apparatus 35 through an interface.

Here, by using, for example, a ball screw of a pitch of 1 mm as the advancing and retreating mechanism part 22, in response to the rotation of the ball screw (that is, the rotation of the stepping motor), the controlling circuit 32 outputs the synchronizing signal M to the record controlling apparatus 34. That is to say, for example, ultrasonic wave images at intervals of 1 mm by outputting the signal once in one rotation or at intervals of 2 mm by outputting the signal once in two rotations can be taken into the auxiliary recording apparatus 35.

Also, the above mentioned auxiliary memorizing apparatus 35 connects a displaying apparatus 36 which can display an image written into or read out of this auxiliary memorizing apparatus 35.

Figure 8:
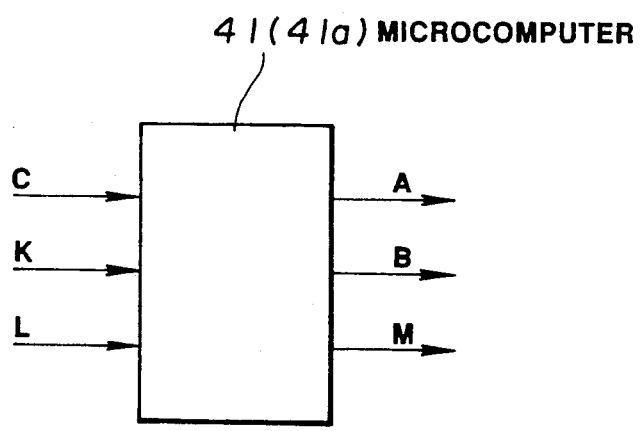

As shown in FIG. 8, the circuit part generating the synchronizing signal M within the above mentioned controlling circuit 32 is formed, for example, of a microcomputer 41.

This microcomputer 41 inputs and counts the phase A signals C output from the encoder 19 and outputs the controlling signals A and B of the stepping motor 23.

Into the microcomputer 41 are input also the signals K and L output by the photointerrupter 26. Whenever these signals K and L are detected, the phases of the controlling signals A and B will be inverted and, when the rotation of the stepping motor 23 is reversed, the advance and retreat of the ultrasonic wave oscillator 11 will be switched over to each other.

Further, the microcomputer 41 produces the synchronizing signal M output to the record controlling apparatus 34 and synchronized with the phase A signal C and signals K and L.

Figure 9:
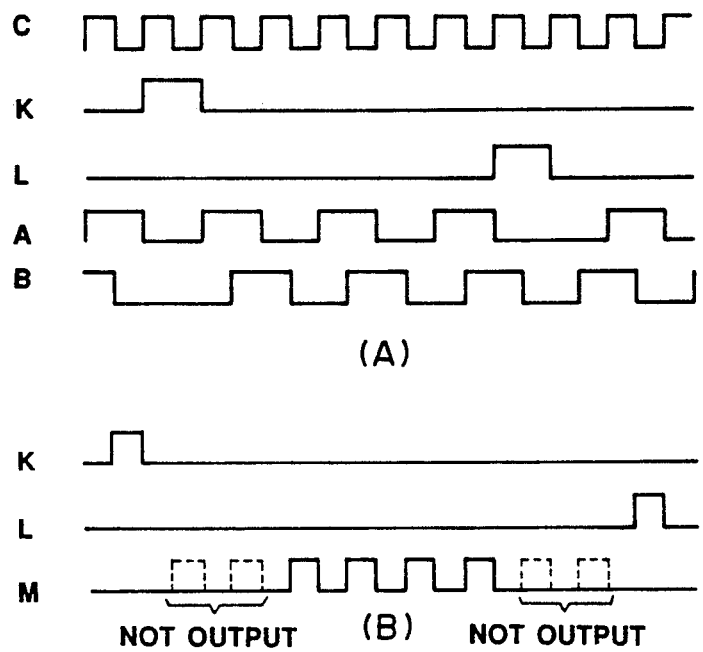

The timings of these phase A signal C, signals K and L and synchronizing signal M are shown in FIG. 9.

As shown in FIG. 9(A), the microcomputer 41 counts the phase A signal C and outputs the controlling signals A and B, will output the signal K when the advancing and retreating motion transmitting part 21 reaches the tip of the advancing and retreating mechanism part 22 and will output the signal L when the advancing and retreating motion transmitting part 21 reaches the rear end of the advancing and retreating mechanism part 22. Also, when the signal K or L is detected, the microcomputer 41 will invert the phases of the controlling signals A and B. Further, as shown by the broken lines in FIG. 9(B), at the beginning and end of the linear scanning, the microcomputer 41 will not output the synchronizing signal M.

The operation of the thus formed ultrasonic wave diagnosing apparatus of the third embodiment shall be explained.

When the advancing and retreating motion transmitting part 21 is detected to have moved to both end parts of the advancing and retreating mechanism part 22, the photointerrupters 26 fixed in the positions corresponding to both ends of the advancing and retreating mechanism part 22 will transmit the signal L or K to the microcomputer 41 which will invert the phases of the controlling signals A and B with the signal K or L. As a result, the rotation of the stepping motor 23 controlled by the controlling signal A or B will be reversed and the advance and retreat of the ultrasonic wave oscillator 12 will be controlled.

On the other hand, as the microcomputer 41 will not output the synchronizing signal M at the beginning and end of the linear scanning, the record controlling apparatus 34 controlling as synchronized with this synchronizing signal M will stop transmitting a writing in command through the interface to the auxiliary memorizing apparatus 25 in this period.

Therefore, if the linear scanning range is, for example, about 30 mm, the output of the synchronizing signal M will be stopped in a range of 5 mm of each end of the linear scanning. When the recording range in the auxiliary recording apparatus is made about 20 mm, regular interval ultrasonic wave images will be able to be recorded without being influenced by the extension and contraction of the drive transmitting part 13.

Thus, according to the fourth embodiment, as ultrasonic wave images irregular in the intervals between the beginning and end of the linear scanning are not recorded in the auxiliary recording apparatus 25, only the ultrasonic wave images arranged at regular intervals can be recorded in the auxiliary recording apparatus 35.

Figure 10:
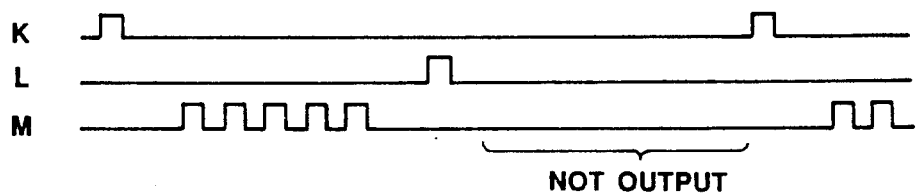

By the way, the timing of the input and output signals of the microcomputer 31 is made as in FIG. 9 but is not limited to this but may be of such timing chart as is shown, for example, in FIG. 10.

That is to say, only the timing of the synchronizing signal M produced by the microcomputer 41 shown in FIG. 9 is different but the timing of the other signals is the same as in FIG. 9 and therefore shall not be explained here.

That is to say, as shown in FIG. 10, the microcomputer 41a (See FIG. 10) of the first modification will output a synchronizing signal M' during the period since the position detecting signal K of the photointerrupter 26 is detected until the position detecting signal L is detected (during the period while the ultrasonic wave oscillator 12 is advancing in the direction away from the tip) but will not output the synchronizing signal M' during the period since the signal L is detected until the signal K is detected (during the period while the ultrasonic wave oscillator 12 advances toward the tip).

In the ultrasonic wave diagnosing apparatus provided with such microcomputer 41a of the first modification, only in the case that the ultrasonic wave oscillator 2 is advancing in the direction away from the tip, ultrasonic wave images will be recorded in the auxiliary recording apparatus 35 in which therefore the ultrasonic wave images will be recorded always in the order from the tip side. Therefore, the direction in which the images are arranged will not become unknown and the three-dimensional image will be able to be processed.

By the way, only in the period while the ultrasonic wave oscillator 2 advances toward the tip, ultrasonic wave images may be recorded in the auxiliary recording apparatus 35.

Figure 11:
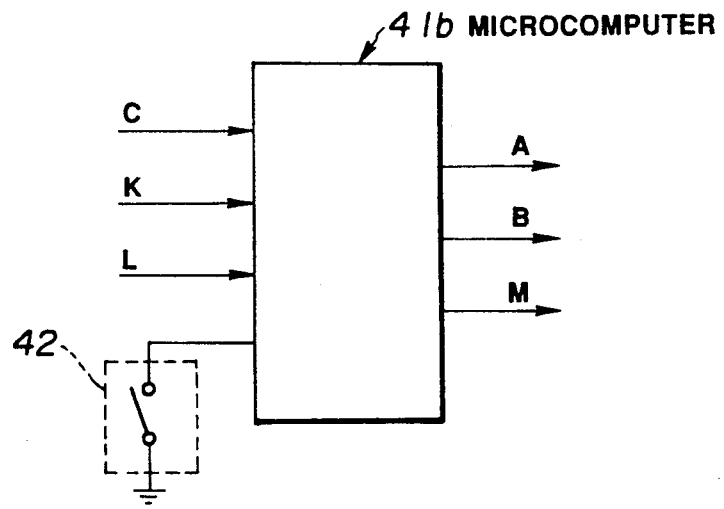

Further, in the microcomputer 41b of the second modification, as shown in FIG. 11, only a part of the signals input into the microcomputer 41 shown in FIG. 8 is different.

That is to say, a linear scanning stopping switch 42 is connected to a microcomputer 41b so that, in case this linear scanning stopping switch 42 is on, the controlling signals A and B and synchronizing signal M will be output but, in case it is off, the controlling signals A and B and synchronizing M will be stopped.

Therefore, in case the linear scanning is stopped and the ultrasonic wave image of the same cross-section is being seen, this image will not be recorded in the auxiliary recording apparatus by switching of f the linear scanning stopping switch 32 and therefore the recording area of the auxiliary recording apparatus will not be uselessly consumed.

By the way, the circuit part generating the synchronizing signal within the controlling circuit 32 is formed of the microcomputer 41 or microcomputers 41a and 41b but, without being limited to them, may be formed, for example, of a PLD or a TTL circuit.

The fourth embodiment shall be explained in the following.

The fourth embodiment is substantially the same as the third embodiment, therefore only the different parts shall be explained and the same parts shall bear the same reference numerals as in the third embodiment and shall not be explained here.

Figure 12:
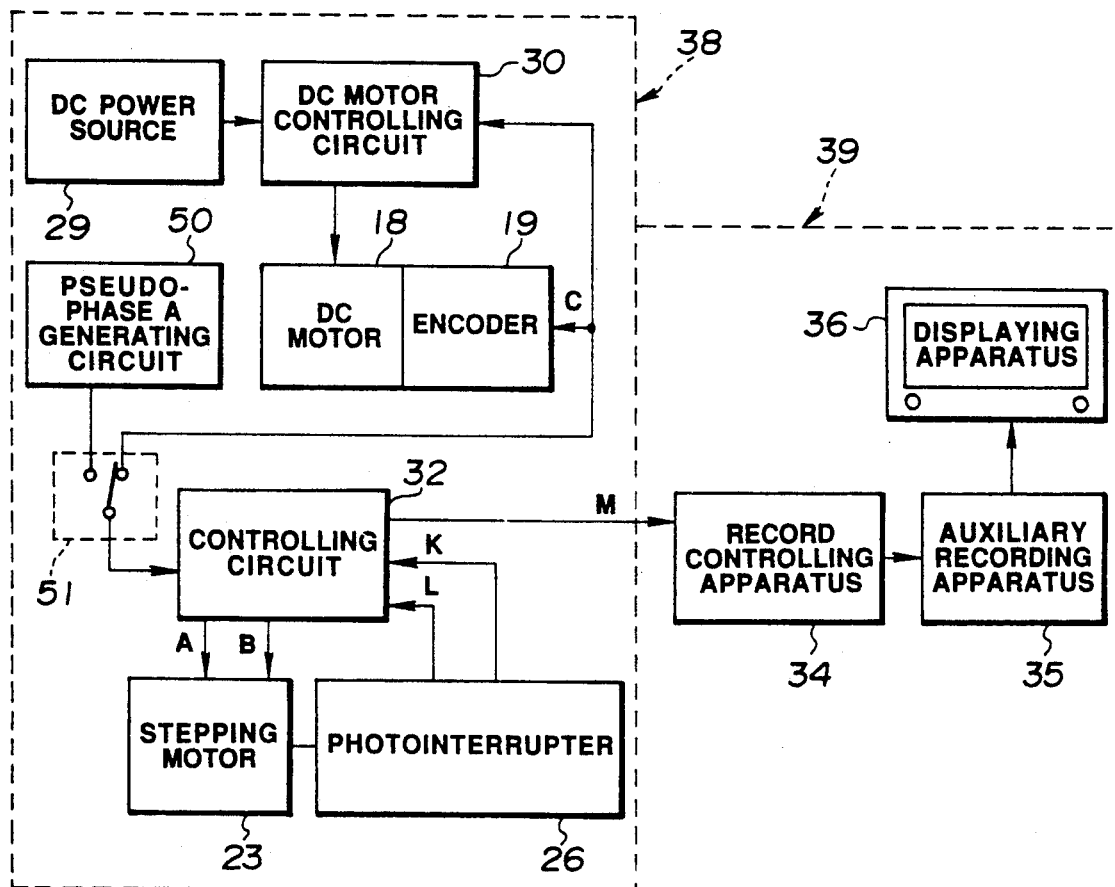
FIG. 12 is a block diagram showing an ultrasonic wave probe controlling system relating to the fourth embodiment.

As shown in FIG. 12, the ultrasonic wave diagnosing apparatus controlling system of the fourth embodiment is provided with a pseudo-phase A generating circuit 50 having as built-in an oscillator not illustrated wherein, even if the rotation of the DC motor 18 is stopped, a pseudo-phase A signal will be able to be generated. The pseudo-phase A signal generated by this pseudo-phase A generating circuit 50 is input into a switching circuit 51 which switches the pseudo-phase A signal to a phase A signal which can be input into the controlling circuit 32.

That is to say, as operatively connected with the stop of the rotation of the DC motor 18, the switching circuit 51 switches the pseudo-phase A to the phase A.

According to the fourth embodiment, even if the radial scanning is stopped, the scanning will be possible with only the linear scanning.

The other formations, operations and effects are the same as in the third embodiment.

The fifth embodiment shall be explained in the following.

Figure 13:
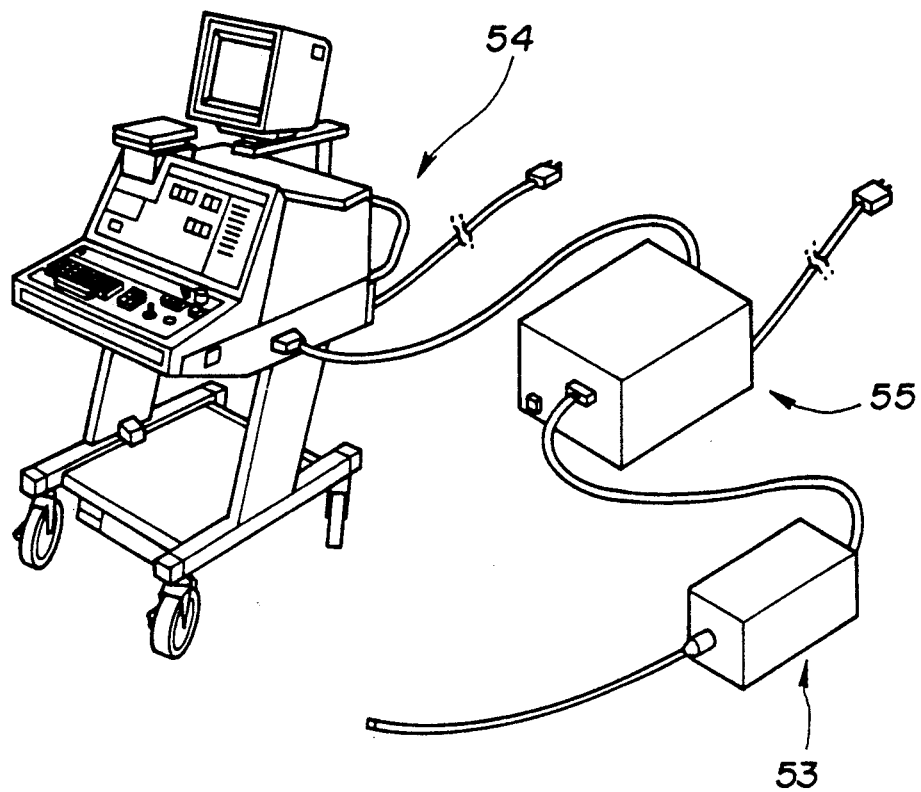
FIGS. 13 and 14 relate to the fifth embodiment.

As shown in FIG. 13, the ultrasonic wave diagnosing apparatus of the fifth embodiment comprises a drive controlling apparatus 53 and image record controlling apparatus 54 forming a conventional mode B displaying ultrasonic wave diagnosing apparatus and a three-dimensional scanning apparatus 55 comprising a three-dimensional scanning controlling part and three-dimensional scanning driving part not illustrated.

Figure 14:
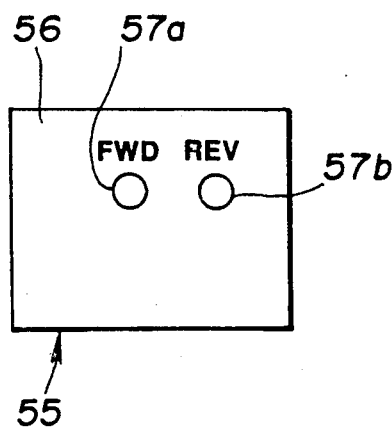

Also, as shown in FIG. 14, indicator lamps 57a and 57b are provided on a surface panel 56 of the three-dimensional scanning apparatus 55. In case the ultrasonic wave oscillator 12 advances and retreats in the linear scanning, during the period while the ultrasonic wave oscillator 12 (See FIG. 5) advances toward the tip part, the indicator lamp 57a will be lighted but the indicator lamp 57b will be extinguished. On the contrary, during the period while the ultrasonic wave oscillator 12 retreats from the tip part, the indicator lamp 57a will be extinguished but the indicator lamp 57b will be lighted.

According to the ultrasonic wave diagnosing apparatus of the fifth embodiment, as the three-dimensional scanning apparatus 55 is connected to the conventional mode B displaying ultrasonic wave diagnosing apparatus, a three-dimensional scanning controlling part and driving part of this three-dimensional scanning apparatus 55 will be added and the three-dimensional scanning will be possible. Therefore, it is not necessary to buy a new three-dimensional ultrasonic wave diagnosing apparatus and it is economical. Also, no space for setting a new diagnosing apparatus is required.

Also, when the insertable part of the ultrasonic wave probe 11 (See FIG. 5) is inserted into a body cavity, even if the advancing and retreating state of the ultrasonic wave oscillator 12 can not be confirmed by sight, it will be able to be confirmed by means of the indicator lamps 57a and 57b and therefore the advance and retreat of the ultrasonic wave oscillator 2 can be made to correspond to the variation of the image.

The other formations, operations and effects are the same as in the third embodiment.

The sixth embodiment shall be explained in the following.

Figure 15:
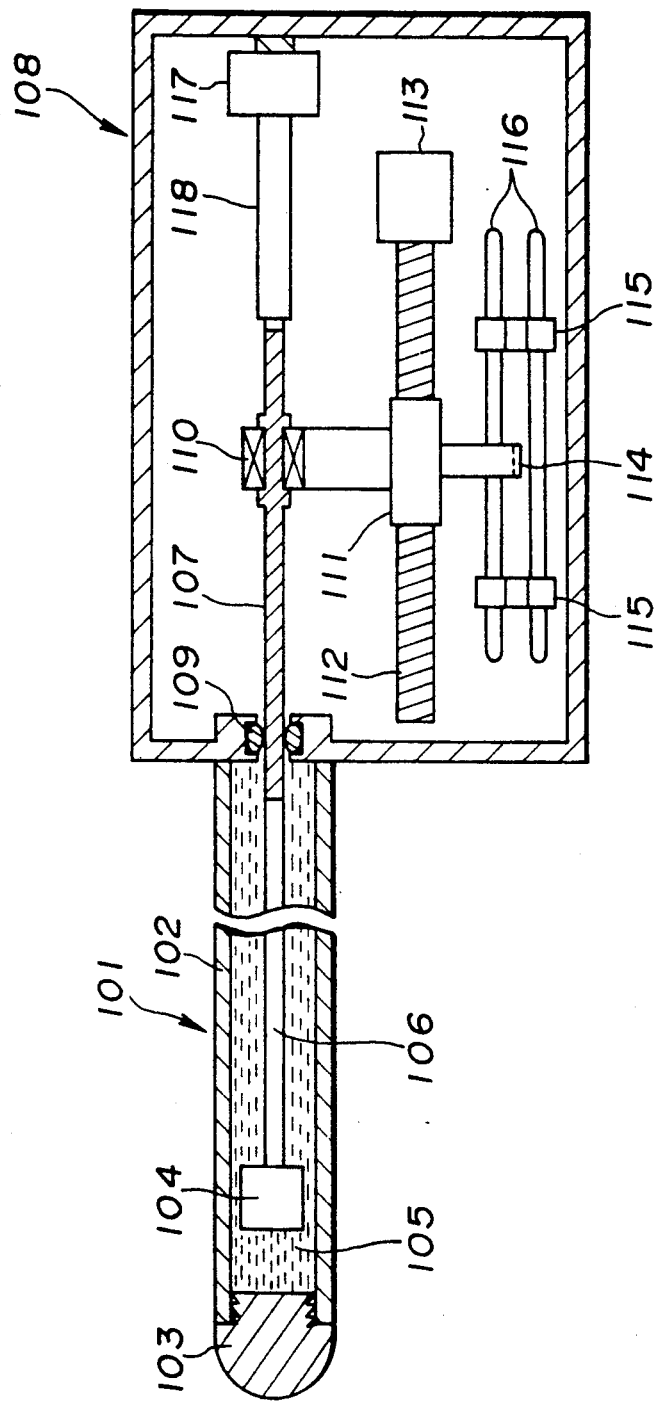
FIGS. 15 to 20 relate to the sixth embodiment.

As shown in FIG. 15, in the ultrasonic wave probe 101 of the ultrasonic wave diagnosing apparatus of the fourth embodiment, a tip frame 103 is secured to the tip of a flexible sheath 102 passing ultrasonic waves to tightly close the interior of the above mentioned sheath 102 and such ultrasonic wave transmitting medium 108 as paraffin in such amount as dips at least all of a housing 104 built-in within the tip part is enclosed. The above mentioned housing 104 holds a later described ultrasonic wave oscillator unit 124, is made slidably adjacent to the inside diameter surface of the above mentioned sheath 102 and is fitted in the end part with a flexible shaft 106.

By the way, the above mentioned sheath 102 is is predetermined in the length so that, when the above mentioned housing 104 has advanced most, a space, for example, of about several mm will be made between the above mentioned housing 104 and tip frame 103 and that, in case the above mentioned sheath 102 is bent, the above mentioned flexible shaft 106 will be prevented from becoming relatively longer than the above mentioned sheath lest the above mentioned tip frame 103 and housing 104 should collide with each other.

Also, a front shaft 107 is fitted to the above mentioned flexible shaft 106 on the rear end side and is inserted into a scanning driving part 108, is held by such elastic holding member 109 as, for example, an O-ring and is held through a bearing 110 by a supporting member 111 provided within the above mentioned scanning driving part 8.

The above-mentioned supporting member 111 is meshed with a ball screw 112 which is fitted on the rear end side to the shaft of a linear scanning motor 113. Also, the above-mentioned supporting member 111 is fitted with a switching member 114 for switching on-/off photocouplers (photointerrupters) 115. The photocouplers 115 for determining the advancing and retreating range, that is, the linear scanning range of the above mentioned housing 104 are fitted on both sides of this switching member 114.

The above-mentioned photocoupler 115 can be fixed in any position by being screwed in two places, for example, from the back side in two elliptic fitting holes 116 provided in parallel along the above-mentioned ball screw 112.50 that the linear scanning range may be properly set.

By the way, the above-mentioned switching member 114 is bent in the end part in the above mentioned fitting hole 116 direction as indicated by the broken line in the drawing so that, when this end part enters the space between the light emitting part and light receiving part of the above mentioned photocoupler 115. a position detecting signal will be output from the above-mentioned photocoupler 115.

A hollow rear shaft 118 borne by bearings 121 (not illustrated in FIG. 15) is connected to the rotating shaft of the radial scanning motor 117 and the above mentioned front shaft 107 is slidably inserted through this rear shaft 118.

Figure 16:
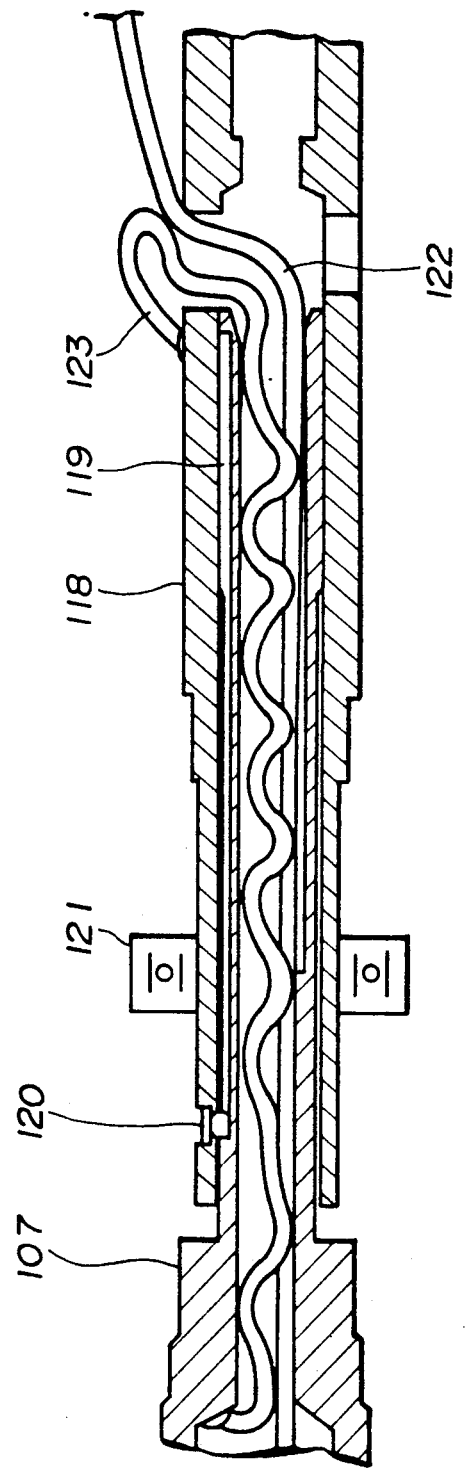

As shown in FIG. 16, the above mentioned front shaft 107 is provided with a key way 119 with which is meshed a key 120 fitted to the above mentioned rear shaft 118 so that the rotation of the above mentioned radial scanning motor 117 may be transmitted to the above mentioned front shaft 107 from the above mentioned rear shaft 118 and that the above mentioned front shaft 107 may be advanced and retreated by sliding through the above mentioned rear shaft 118 by the above mentioned rear scanning motor 113.

By the way, the above mentioned front shaft 107 and rear shaft 118 are formed of a conductive material and are grounded. Further, a coaxial cable 122 and grounding strengthening cable 123 connected to an ultrasonic wave oscillator unit 124 are inserted through the above mentioned front shaft 107 and rear shaft 118. The above mentioned grounding strengthening cable 123 is connected at both ends respectively to the above mentioned front shaft 107 and rear shaft 118 by soldering or the like so that the above mentioned front shaft 107 and rear shaft 118 may be kept at the same potential, the grounding may be strengthened and the noise may be reduced.

Figure 17:
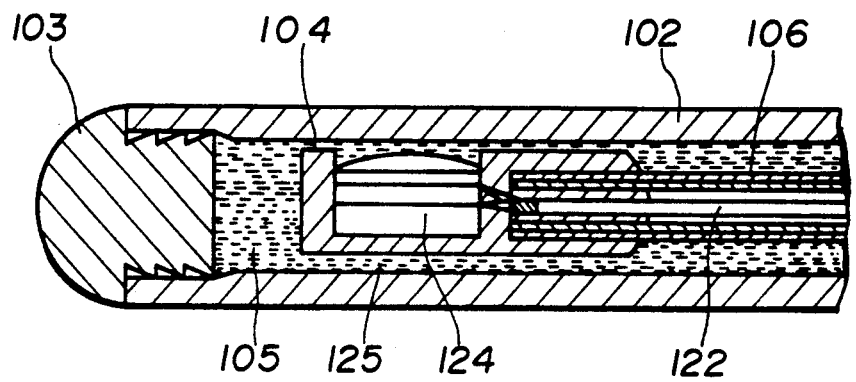

As shown in FIG. 17, on the other hand, the ultrasonic wave oscillator unit 124 having a piezo-electric device, matching layer and suction layer and radiating ultrasonic waves when excited is built-in and held in the above mentioned housing 104 and is fixed with the ultrasonic wave radiating surface directed outside to the above mentioned housing 104 made, for example, of stainless steel or the like.

The above mentioned coaxial cable 122 is connected to the above mentioned ultrasonic wave oscillator unit 124, is inserted through the above mentioned flexible shaft 106 fixed by a bonding agent or the like in a hole provided in the end part of the above mentioned housing 104, is further inserted through the above mentioned front shaft 107 and rear shaft 118 and is connected at the end to an ultrasonic wave observing apparatus not illustrated through the above mentioned scanning driving part 108.

Figure 18:
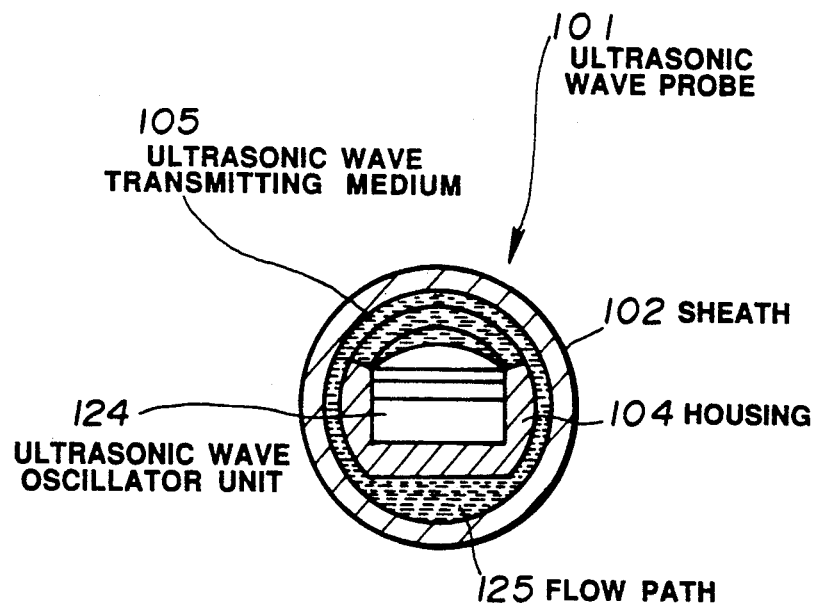

As shown in FIG. 18, the above mentioned housing 104 has the outside diameter surface adjacent to the inside diameter surface of the above mentioned sheath 102 to have a clearance, for example, of about 1 mm. but, on the other hand, is cut off in the lengthwise direction on the side opposite the ultrasonic wave radiating surface of the above mentioned ultrasonic wave oscillator unit to form a flow path 125 for flowing the ultrasonic wave transmitting medium 105 before and after in the lengthwise direction of the above mentioned housing 104.

The other formations are the same as in the third embodiment.

In the ultrasonic wave probe 101 of the ultrasonic wave diagnosing apparatus of the sixth embodiment by the above formation, when an electric power, for example, of several $MH_z$ to several ten $MH_z$ is fed through the coaxial cable 122 from the ultrasonic wave observing apparatus not illustrated, the ultrasonic wave oscillator unit 124 will be excited to radiate ultrasonic waves to an object to be examined.

The ultrasonic waves reflected by the object are received by the above mentioned ultrasonic wave oscillator unit 124, the signal from this ultrasonic wave oscillator unit 124 is processed by the ultrasonic wave observing apparatus not illustrated and a cross-sectioned image of the examined object is displayed in a monitor not illustrated.

By the way, at this time, as the grounding of the front shaft 107 and rear shaft 118 through which the above mentioned coaxial cable 122 is inserted is strengthened by the grounding strengthening cable 123, the noise will be greatly reduced.

Here, if the radial scanning motor 117 is rotated, the rotation will be transmitted to the front shaft 107 from the rear shaft 118 through the key 120 and key way 119, the housing 104 fixed to the flexible shaft 106 will rotate and ultrasonic waves will be radiated in the direction intersecting at right angles with the axis of the sheath 102 from the above mentioned ultrasonic wave oscillator unit 124 held by the housing 104 to make a radial scanning.

Also, when the linear scanning motor 113 is rotated, the ball screw 112 will rotate and the supporting member 111 meshed with this ball screw 112 will make a straight advancing motion. As a result, the above mentioned housing 104 will move in the axial direction of the above mentioned sheath 102 through the above mentioned front shaft 107 and, when the end part of the switching member 114 enters the space between the light emitting part and light receiving part of the photocoupler 115 and a position detecting signal is output, the rotating direction of the above mentioned linear scanning motor 113 will be reversed by this position detecting signal and the above mentioned housing 104 will repeat the advancing and retreating motion within the linear scanning range.

In this case, the ultrasonic wave transmitting medium 105 will flow around the housing 104 through the flow path 125, therefore the movement of the housing 104 will not be obstructed, the above mentioned housing 104 will smoothly move and the linear scannability will greatly improve. Further, when the above mentioned linear scanning motor 113 and radial scanning motor 117 are simultaneously rotated, the above mentioned housing 104 will spirally move and a spiral scanning will be able to be realized. In the case of making any of the radial scanning, linear scanning and spiral scanning, the ultrasonic wave transmitting medium 105 interposed between the sheath 102 and housing 104 will become a lubricant, the ultrasonic wave oscillator unit 124 held by the housing 104 will be able to make the scanning without deflecting with respect to the sheath 102 and a clear ultrasonic wave image will be able to be obtained.

The other operations and effects are the same as in the third embodiment.

Figure 19:
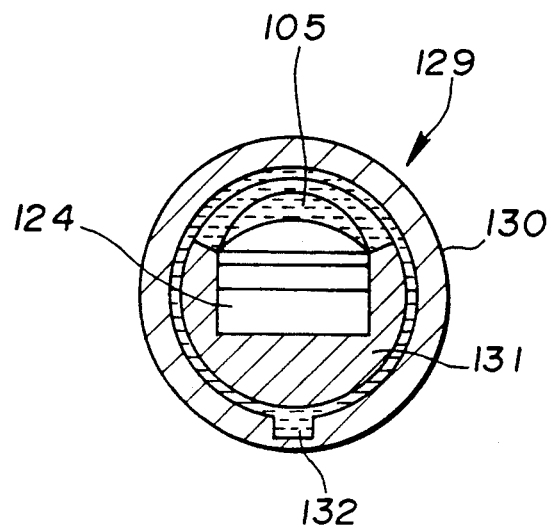

By the way, here, an ultrasonic wave probe of the first modification of the sixthh embodiment shall be shown in FIG. 19. In the ultrasonic wave probe of the first modification in the following, the same components as of the ultrasonic wave probe of the above described fourth embodiment shall bear the same reference numerals and shall not be explained here.

In the ultrasonic wave probe 129 of the first modification, as shown in FIG. 19, the sheath 102 in the above described fourth embodiment is made a sheath 130 having a groove formed on the inner peripheral surface and a flow path 132 for the ultrasonic wave transmitting medium 105 is formed of this groove.

That is to say, a cylindrical housing 131 holding the ultrasonic wave oscillator unit 124 is made slidably adjacent to the inside diameter surface of the sheath 130, on the other hand, a groove is made on the inner peripheral surface of the above mentioned sheath 130 on the side opposite the ultrasonic wave radiating surface of the above mentioned ultrasonic wave oscilator unit 124 and the flow path 132 for the ultrasonic wave transmitting medium 105 is formed of this groove.

The above mentioned flow path 132 is properly formed in the lengthwise direction of the above mentioned sheath 130 so as to be linear, spiral or snaky. It is needless to say that, even in the ultrasonic wave probe of the second modification by such formation, the same operations and effects as of the ultrasonic wave probe of the above described first embodiment can be obtained.

Figure 20:
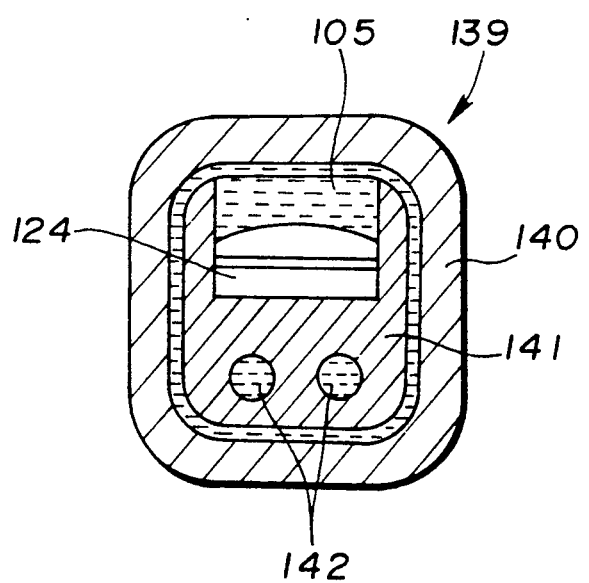

Further, the ultrasonic wave probe of the second modification is shown in FIG. 20.

The ultrasonic wave probe 139 of the second modification is a linear scanning type ultrasonic wave probe in which the cross-section in the direction intersecting at right angles with the axial direction of the sheath 140 is substantially square, a housing 141 of a substantially square cross-section is made slidably adjacent to the inside surface of the above mentioned sheath 140 and the ultrasonic wave oscillator unit 124 is held.

In the above mentioned housing 141, through holes passing through the above mentioned housing 141 are made on the side opposite the ultrasonic wave radiating surface of the above mentioned ultrasonic wave oscillator unit 124 and flow paths 142 for the ultrasonic wave transmitting medium 105 are formed of these through holes.

In such formation, in case the housing 141 moves in the axial direction of the sheath 140, the ultrasonic wave transmitting medium 105 will flow through the flow paths 142, not only a smooth linear scanning will be able to be realized but also the ultrasonic wave oscillator unit 124 will not displace in the rotating direction and therefore an adapted linear scanning will be able to be realized.

By the way, in the ultrasonic wave probe of the second modification, the other members not illustrated can be also adapted to the linear scanning and the sheath 140 and housing 141 are not limited to be substantially square but can be properly selected to be of such shape which can suppress the displacement in the rotating direction as a polygon or ellipse. Further, it is needless to say that the flow path 142 for the ultrasonic wave transmitting medium 105 is not limited to be circular but can be properly selected to be of such shape as a square or ellipse.

The seventh embodiment shall be explained. By the way, an ultrasonic wave diagnosing apparatus of a mechanical linear scanning system is shown in the drawing.

Figure 21:
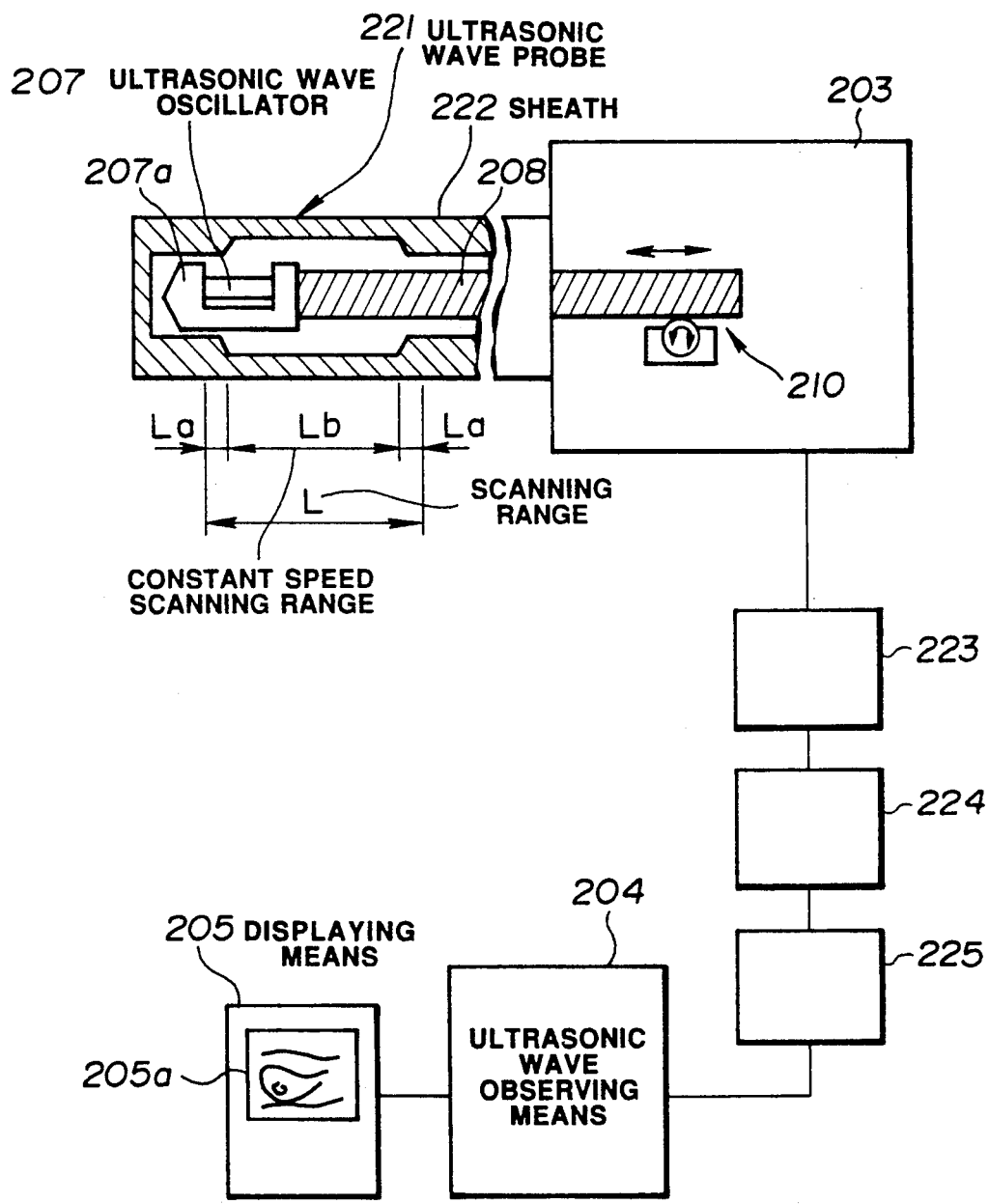

In the ultrasonic wave diagnosing apparatus of the seventh embodiment, as shown in FIG. 21, the reference numeral 221 in the drawing represents an ultrasonic wave probe, and a long flexible sheath 222 forming this ultrasonic wave probe 221 is connected at the base end to the driving part 203. A housing 207a in which an ultrasonic wave oscillator 207 is fixed and provided is contained in the tip part of this sheath 222 so as to be reciprocatable along the above mentioned sheath and is connected to a reciprocating motion mechanism 210 provided in the above mentioned driving part 203.

The reference numeral 223 represents a multiplex echo detecting means detecting echoes received by the above mentioned ultrasonic wave oscillator 207.

The reference numeral 224 represents a multiplex echo judging means timing the intervals of the echoes detected by the above mentioned multiplex echo detecting means 223 and judging whether the scanning direction of the ultrasonic wave oscillator 207 is in the reciprocation reversing range or not.

The reference numeral 225 represents a controlling means which will transmit a received signal to an ultrasonic wave observing means 204 only when the ultrasonic wave oscillator 207 is judged by the above mentioned multiplex echo judging means 224 to be scanning a range than the reciprocation reversing range other, that is, to be scanning a constant speed scanning range Lb. By the way, the reference numeral 205 represents a television monitor which is an example of a displaying means.

Figure 22:
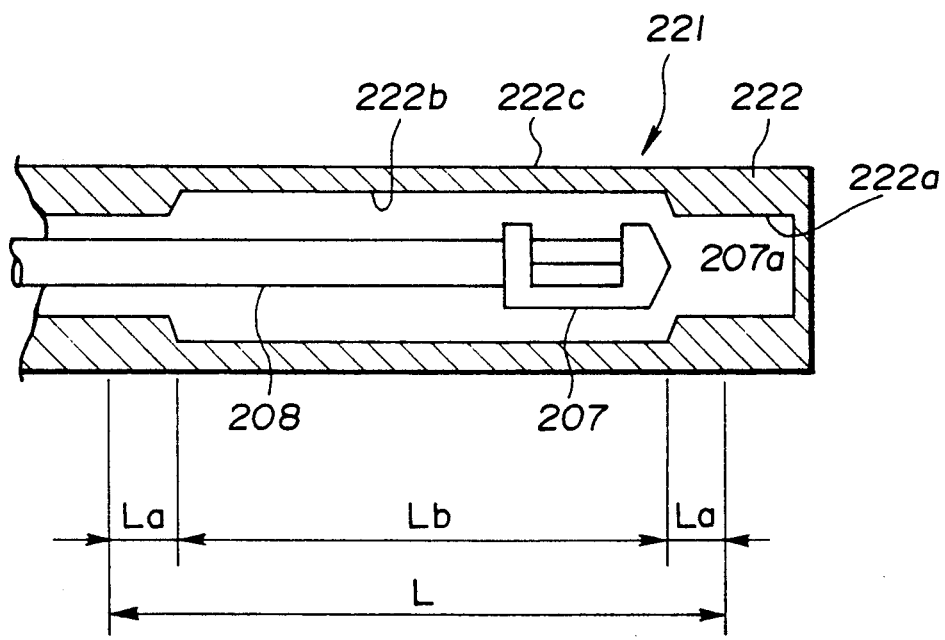

In the tip part of the above mentioned sheath 222, as shown in FIG. 22, the above mentioned ultrasonic wave oscillator 207 reciprocates, makes the ultrasonic wave beam scan in the region of the range L and is set in the position where the inside surface 222b in the range (constant speed scanning range) Lb of the above mentioned scanning range L of the inside surface 222a of the above mentioned sheath 228 excepting both end parts La is away from the above mentioned ultrasonic wave oscillator 207 (in the drawing, it is away by reducing the thickness in only the constant speed scanning range Lb). By the way, the outside surface 222c of the above mentioned sheath 222 is formed to be of the same diameter.

The other formations are the same as in the third embodiment.

The operation of the seventh embodiment by the above mentioned formation shall be explained in the following.

Figure 23:
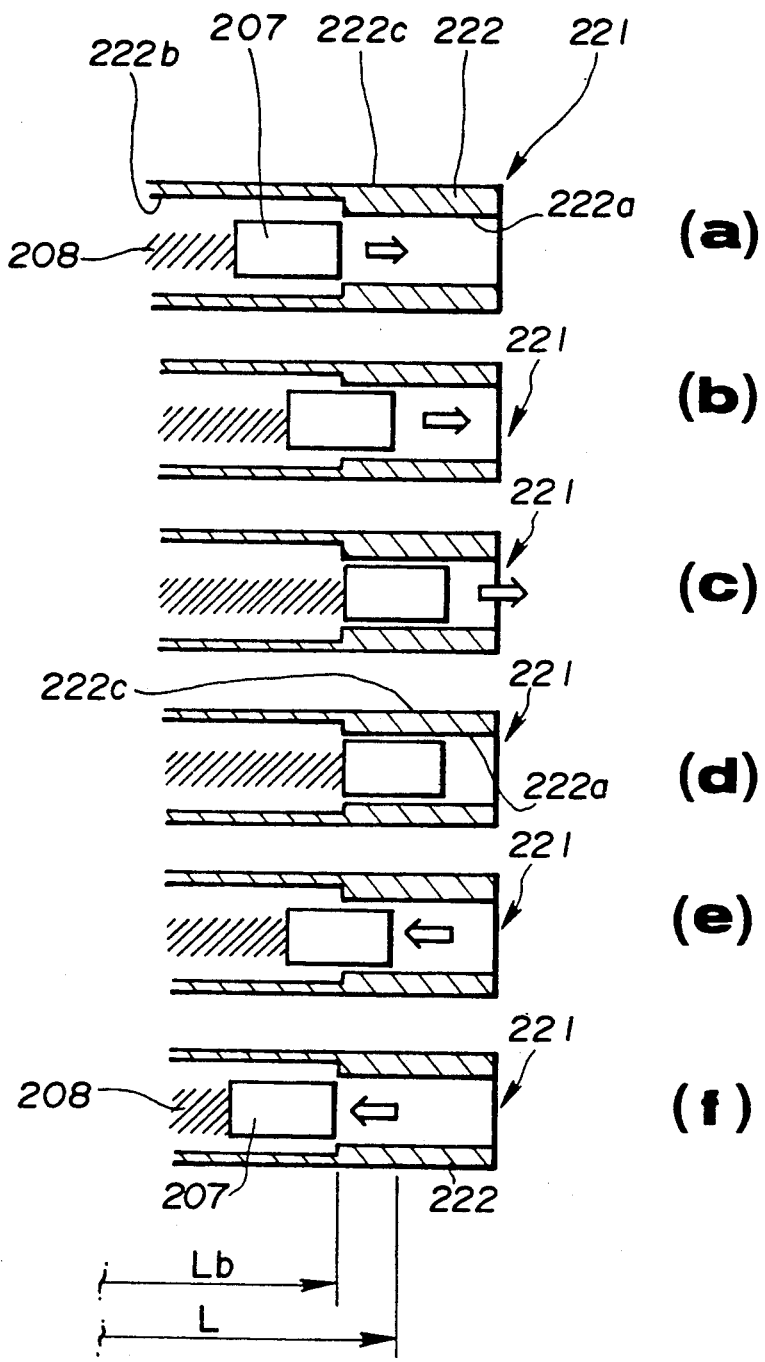
Figure 24:
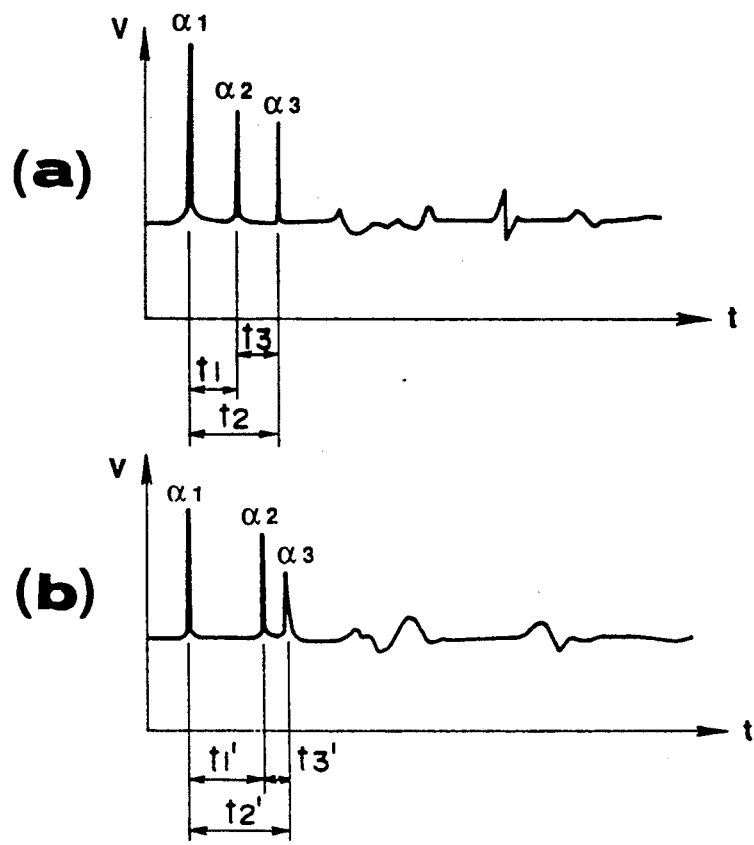

As shown in FIG. 23(d), when the ultrasonic wave oscillator 207 is in the region where the scanning direction is reversed near the ending end of the scanning range L, as shown in FIG. 24(a), after the elapsing time of t1 from the emitted pulse α1 of the ultrasonic wave oscillator 207, an echo α2 from the inside surface 222a of the sheath 222 will be received and, after the elapsing time of t2, an echo α3 from the outside surface 222c of the sheath 222 will be received. Therefore, the time difference between the echoes α2 and α3 is t3.

On the other hand, as shown in FIGS. 23(a) and (f), when the above mentioned ultrasonic wave oscillator 207 is scanning at a constant speed, as shown in FIG. 24(b), after the elapsing time of t1', an echo α2 from the inside surface 222b of the sheath 222 will be received and, after the elapsing time of t2', an echo α3 from the outside surface 222 will be received.

As the inside surface 222b in the constant speed scanning range Lb in the above mentioned sheath 222 is in the position farther from the ultrasonic wave oscillator 207 than the inside surfaces 222a at both ends, that is to say, as this inside surface 222b is in the position near to the outside surface 222c, the time difference t3' between the echoes α2 and α3 will be shorter than the time difference t3 during the reversal of the above mentioned scanning direction (t3'<t3).

Therefore, the time difference between the echoes α2 and α3 detected by the multiplex echo detecting means 223 is judged by the multiplex echo judging means 224. Only when this time difference is t3', the time difference of t3' will be judged to be in the constant speed scanning range Lb and the signal received by the above mentioned ultrasonic wave oscillator 207 from the controlling means 225 will be transmitted to the ultrasonic wave observing means 204.

As a result, in the television monitor 205, the image 205a of only the range Lb in which the ultrasonic wave oscillator 207 is scanning at a constant speed is displayed and the image flows at the time of the reversal are cut.

Also, as substantially the position of the ultrasonic wave oscillator 201 is directly detected in the tip part of the ultrasonic wave probe 221, the image 25 will not move to the right and left with the reciprocation.

By the way, in this seventh embodiment, the received signal input into the ultrasonic wave observing means 204 is made intermittent but it is needless to say that the entire wiring is not limited to it and, for example, the output signal of the ultrasonic observing means 4 may be made intermittent.

The other operations and effects are the same as in the third embodiment.

The eighth embodiment shall be explained in the following. By the way, in the drawing is shown an ultrasonic wave diagnosing apparatus of a mechanical linear scanning system.

Figure 25:
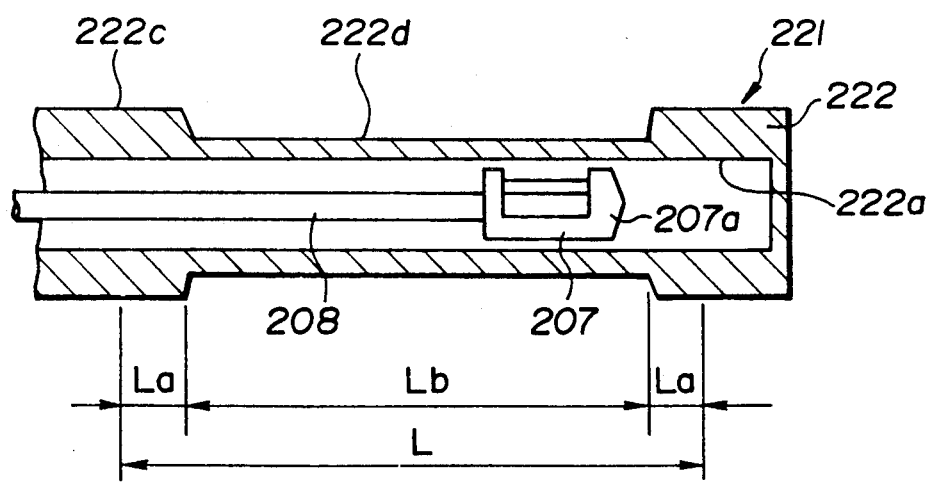
FIGS. 25 and 26 relate to the eighth embodiment of the present invention.
Figure 26:
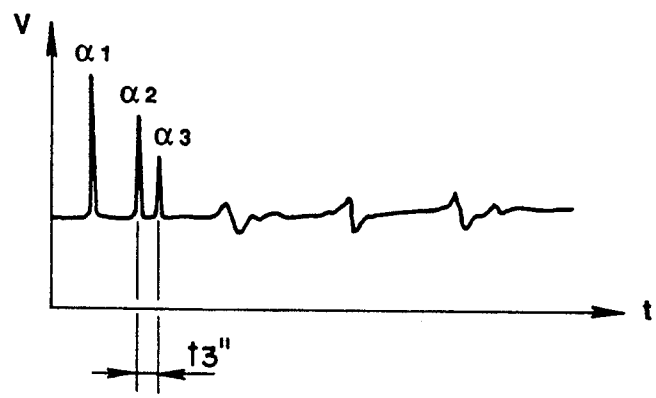

The eighth embodiment is substantially the same as the seventh embodiment. That is to say, in this eighth embodiment, as shown in FIG. 25, the inside surface 222a of the sheath 222 is of the same diameter and the part 222d corresponding to the constant speed scanning range Lb of the outside surface 222c is set in the position (in the drawing, the thickness is reduced) adjacent to the above mentioned inside surface 222a. As shown in FIG. 26, as the time difference t3'' between the echo α2 from the inside surface 222a of the sheath 222 and the echo α3 from the outside surface 222d is shorter than the time difference t3 (See FIG. 24(a)) between the echo α2 from the inside surface 222a and the echo α3 from the outside surface 222c as detected at both ends La, when this time difference t3'' is detected, the image signal may be transmitted.

According to this eighth embodiment, as the inside surface 222a of the sheath is of the same diameter, the eccentricity of the ultrasonic wave oscillator 207 at the time of scanning will be minimum and, as the outside surface 222d may be worked, it will be easy to mold.

By the way, in the constant speed scanning range Lb, lest another higher order multiplex echo should be interposed between the echoes α2 and α3, it is desirable to set the ratio of the inside diameter to the outside diameter of the sheath 222 at a value near to 1:1.

Also, the shape of the constant speed scanning range Lb of the sheath 222 is not limited to those of the above mentioned respective embodiments but may be a shape in which the manner of the echo from the sheath 222 is different from those of other parts.

The other formations, operations and effects are the same as in the seventh embodiment.

The ninth embodiment shall be explained in the following. By the way, in the drawing is shown an ultrasonic wave diagnosing apparatus of a mechanical linear scanning system.

Figure 27:
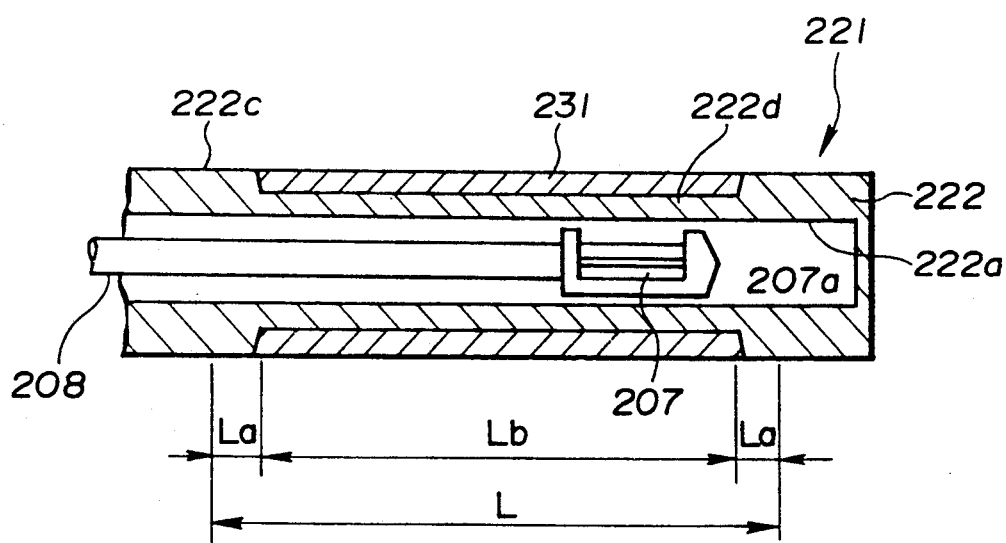
FIG. 27 relates to the ninth embodiment of the present invention and is a longitudinally sectioned view of the tip part of the ultrasonic wave probe corresponding to FIG. 22.

The ninth embodiment is substantially the same as the eighth embodiment. That is to say, as shown in FIG. 27, in this embodiment, the outside surface 222d in the constant speed scanning range Lb of the sheath 222 of the above described eighth embodiment is charged with a charging member 231 to flatten the outside surface of this sheath 222 so that the ultrasonic wave probe 221 may be easy to insert.

The above mentioned charging member 231 is made of a material having an acoustic impedance different from that of the above mentioned sheath 222 so that the echo α3 of the outside surface 222d of the above mentioned sheath 222 may be detected the same as in the above mentioned seventh embodiment.

The other formations, operations and effects are the same as in the seventh embodiment.

By the way, if the seventh to ninth embodiments are adopted not only in the ultrasonic wave diagnosing apparatus of the mechanical linear scanning system but also in such spiral scanning type ultrasonicwave diagnosing apparatus for obtaining three-dimensional images as is shown, for example, in FIG. 28, the image at the time of the reversal in the linear system component will be able to be easily processed. By the way, the reference numeral 241 represents a motor driving the ultrasonic wave oscillator 207 in the radial direction.

Also, if those embodiments are adopted in such mechanical sector system ultrasonic wave diagnosing apparatus as is shown in FIG. 29, the image at the time of the reversal in the rocking motion will be able to be easily processed. By the way, the reference numeral 251 represents the gums to be diagnosed.

By the way, the ultrasonic wave diagnosing apparatus by the present invention is considered to be applied as shown in FIG. 30. That is to say, when an affected part 262 of a tube cavity 261 is to be cauterized and removed with a laser probe 264 by using a through endoscope 263, if the cauterization is advanced while observing the cross-sectioned shape of the affected part with the ultrasonic wave probe 221 of the ultrasonic wave diagnosing apparatus according to the present invention, the above mentioned tube cavity 261 will be able to be prevented from being holed.

Further, if such reflective coating as a white painted film 265 is applied to the surface 222c of the sheath 222 of the above mentioned ultrasonic wave probe 221 as shown in FIG. 31, the ultrasonic wave probe 221 will be able to be prevented from being broken by the dispersed laser light. As the part likely to be broken by the laser is only the ultrasonic wave oscillator 207, such reflective coating as a metal film may be only applied to the surface of this ultrasonic wave oscillator 207.

Further, in case the ultrasonic wave diagnosing apparatus is to be applied to a vein, it is necessary that the ultrasonic wave probe 221 should be strictly sterilized. Usually, the devices to be used in a circulatory system are sealed to be sterilized in a dispopack which is used only once. However, if such long device as the ultrasonic wave probe 221 is contained as it is in the dispopack, it will be inconvenient to handle. Therefore, as shown in FIG. 32, the ultrasonic wave probe 221 may be contained as wound like a tape measure in a dispopack 271 so as to be pulled out of the above mentioned dispopack 271 when it is to be used. By the way, in the drawing, the reference numeral 272 represents an external connecting connector.

It is apparent that, in this invention, working modes different in a wide range can be formed on the basis of this invention without deviating from the spirit and scope of the invention.

What is claimed is:

1. An ultrasonic wave diagnosing apparatus, comprising:
   an ultrasonic wave probe having an ultrasonic wave transmitting and receiving part which can be rotated, advanced and retreated and which transmits and receives ultrasonic waves;
   a first driving means rotating said ultrasonic wave transmitting and receiving part;
   a second driving means advancing and retreating said ultrasonic wave transmitting and receiving part;
   an auxiliary recording means recording signals from said ultrasonic wave transmitting and receiving part; and
   a record controlling means outputting to said auxiliary recording means a record controlling signal synchronized with input signals from said first driving means and said second driving means.

2. An ultrasonic wave diagnosing apparatus according to claim 1, further comprising:
   an advance and retreat detecting means detecting the position of said ultrasonic wave transmitting and receiving part in an end part of the advancing and retreating range of said ultrasonic wave transmitting and receiving part, said record controlling means being synchronized with input signals from said first driving means and said second driving means by said advance and retreat detecting means, outputting a record controlling signal controlling and auxiliary recording means and controlling said auxiliary recording means.

3. An ultrasonic wave diagnosing apparatus according to claim 2, further comprising:
   a rotation detecting means detecting the rotation of said first driving means; and
   a drive controlling means controlling said first driving means and said second driving means with said advance and retreat detecting means and rotation detecting means.

4. An ultrasonic wave diagnosing apparatus according to claim 2, where said second driving means is a stepping motor.

5. An ultrasonic wave diagnosing apparatus according to claim 2, wherein said drive controlling means is a microcomputer.

6. An ultrasonic wave diagnosing apparatus according to claim 2, wherein said ultrasonic wave probe has an ultrasonic wave oscillator for transmitting, receiving and scanning ultrasonic wave beams, and a sheath movably containing said ultrasonic wave oscillator, wherein said apparatus is provided with an ultrasonic wave observing means converting the received signal of said ultrasonic wave oscillator to an image signal and a displaying means displaying an ultrasonic wave cross-sectioned image on the basis of said image signal which is formed so that the kind of an echo coming from said sheath in the advancing and retreating range of said ultrasonic wave transmitting and receiving part of said sheath is formed differently from a kind of the echo from another part of said sheath, wherein said ultrasonic wave transmitting and receiving part is disposed in an end part in the advancing and retreating range of the ultrasonic wave transmitting and receiving part is detected by a change of the kind of the echo coming from said sheath.

7. An ultrasonic wave diagnosing apparatus according to claim 6 wherein said sheath is different in the thickness between the advancing and retreating range of said ultrasonic wave transmitting and receiving part and a region other than said range.

8. An ultrasonic wave diagnosing apparatus according to claim 6 wherein said sheath has an acoustic impedance different between the advancing and retreating range of said ultrasonic wave transmitting and receiving part and a region other than said range.

9. An ultrasonic wave diagnosing apparatus according to claim 2, wherein said ultrasonic wave probe is provided in a sheath tip part with a housing holding an ultrasonic wave oscillator unit and made slidably adjacent to said sheath inside diameter surface and with flow paths for flowing an ultrasonic wave transmitting medium around said housing.

10. An ultrasonic wave diagnosing apparatus according to claim 9 wherein said advance and retreat detecting means comprises a light shielding means provided in said ultrasonic wave probe advanced and retreated by said second driving means and a plurality of photodetecting means shielded by said light shield means.

11. An ultrasonic wave diagnosing apparatus according to claim 2, wherein said advance and retreat detecting means comprises a light shielding means provided in said ultrasonic wave probe advanced and retreated by said second driving means and a plurality of photodetecting means shielded by said light shielding means and detecting when said ultrasonic wave transmitting and receiving part is positioned in an end part of the advancing and retreating range of said ultrasonic wave transmitting and receiving part.

12. An ultrasonic wave diagnosing apparatus according to claim 1, further comprising:
   a pseudo-signal generating means generating a pseudo-signal; and
   a switching means switching a pseudo-signal from said pseudo-signal generating means and a signal from said first driving means over to each other and outputting them to said record controlling means.

13. An ultrasonic wave diagnosing apparatus according to claim 1, further comprising a displaying means displaying a driving state of said second driving means.

14. An ultrasonic wave diagnosing apparatus according to claim 1, further comprising:

an origin position changing means changing the displaying origin position of said ultrasonic wave cross-sectioned image in response to a movement of said ultrasonic wave transmitting and receiving part or a living body signal having a periodicity, said auxiliary recording means consisting of a frame memory for either renewing recording or superimposing recording in the respective corresponding addresses the data relating to said ultrasonic wave cross-sectioned image on the basis of said origin position changing means.

15. An ultrasonic wave diagnosing apparatus according to claim 14, wherein said advance and retreat detecting means comprises a light shielding means provided in said ultrasonic wave probe advanced and retreated by said second driving means and a plurality of photodetecting means shielded by said light shielding means and detecting when said ultrasonic wave transmitting and receiving part is positioned in an end part of the advancing and retreating range of said ultrasonic wave transmitting and receiving part.

16. An ultrasonic wave diagnosing apparatus according to claim 15 wherein, when said photodetecting means detects when said ultrasonic wave transmitting and receiving part is positioned in an end part of the advancing and retreating range of said ultrasonic wave transmitting and receiving part, said drive controlling means will reverse and control the rotation of said first driving means.

17. An ultrasonic wave diagnosing apparatus according to claim 14 wherein, when said advance and retreat detecting means detects when said ultrasonic wave transmitting and receiving part is positioned in an end part of the advancing and retreating range of said ultrasonic wave transmitting and receiving part, said drive controlling means will reverse and control the rotation of said first driving means.

18. An ultrasonic wave diagnosing apparatus according to claim 14, further comprising a signal stopping means letting said record controlling means stop outputting said record controlling signal to said auxiliary recording means in case said drive controlling means stops and controls said second driving means.

19. An ultrasonic wave diagnosing apparatus according to claim 14, wherein said first driving means is a DC motor and said rotation detecting means is an encoder detecting the rotation of said DC motor.

20. An ultrasonic wave diagnosing apparatus according to claim 14, further comprising:
an ultrasonic wave oscillator for transmitting, receiving and scanning ultrasonic wave beams;
an ultrasonic wave observing means having a sheath movably containing said ultrasonic wave oscillator and converting the received waves of said ultrasonic wave oscillator to image signals; and
a displaying means displaying ultrasonic cross-sectioned images on the basis of said image signals, wherein the kind of an echo coming from said sheath in the advancing and retreating range of said ultrasonic wave transmitting and receiving part of said sheath is formed differently from a kind of the echo from another part of said sheath, wherein said ultrasonic wave transmitting and receiving part is disposed in an end part in the advancing and retreating range of the ultrasonic wave transmitting and receiving part is detected by a change of the kind of the echo coming from said sheath.

21. An ultrasonic wave diagnosing apparatus, according to claim 1, wherein a housing holds an ultrasonic wave oscillator unit in a sheath tip part and is slidably adjacent to an inside diameter surface of said sheath having flow paths for flowing an ultrasonic wave transmitting medium around said housing.

* * * * *